(12) United States Patent
Li

(10) Patent No.: US 9,951,335 B2
(45) Date of Patent: *Apr. 24, 2018

(54) COMPOSITIONS AND METHODS FOR TREATING OTITIS MEDIA AND OTHER CONDITIONS WITH INHIBITORS OF CYLD

(71) Applicant: Georgia State University Research Foundation, Inc., Atlanta, GA (US)

(72) Inventor: Jian-Dong Li, Marietta, GA (US)

(73) Assignee: Georgia State University Research Foundation, Inc., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/391,890

(22) PCT Filed: Apr. 9, 2013

(86) PCT No.: PCT/US2013/035863
§ 371 (c)(1),
(2) Date: Oct. 10, 2014

(87) PCT Pub. No.: WO2013/155123
PCT Pub. Date: Oct. 17, 2013

(65) Prior Publication Data
US 2015/0065561 A1 Mar. 5, 2015

Related U.S. Application Data

(60) Provisional application No. 61/622,486, filed on Apr. 10, 2012.

(51) Int. Cl.
| | |
|---|---|
| *A61K 31/277* | (2006.01) |
| *A61K 31/4015* | (2006.01) |
| *A61K 31/44* | (2006.01) |
| *A61K 31/4174* | (2006.01) |
| *A61K 31/685* | (2006.01) |
| *A61K 31/7064* | (2006.01) |
| *C12N 15/113* | (2010.01) |
| *C12Q 1/68* | (2006.01) |
| *A61K 31/713* | (2006.01) |

(52) U.S. Cl.
CPC ........ *C12N 15/1137* (2013.01); *A61K 31/277* (2013.01); *A61K 31/4015* (2013.01); *A61K 31/4174* (2013.01); *A61K 31/44* (2013.01); *A61K 31/685* (2013.01); *A61K 31/7064* (2013.01); *A61K 31/713* (2013.01); *C12Q 1/68* (2013.01); *C12Y 301/04017* (2013.01); *C12N 2310/11* (2013.01); *C12N 2310/14* (2013.01); *C12N 2310/141* (2013.01); *C12Y 304/19012* (2013.01)

(58) Field of Classification Search
None
See application file for complete search history.

(56) References Cited

U.S. PATENT DOCUMENTS

| 6,174,878 | B1 * | 1/2001 | Gamache ............... | A61K 31/55 514/211.12 |
|---|---|---|---|---|
| 2003/0054531 | A1 | 3/2003 | Gretarsdottir et al. | |
| 2006/0041006 | A1 | 2/2006 | Ibrahim et al. | |
| 2006/0084684 | A1 * | 4/2006 | Bolle ................... | A61K 9/0043 514/352 |
| 2006/0100218 | A1 | 5/2006 | Ibrahim et al. | |
| 2007/0167450 | A1 * | 7/2007 | Kobayashi ........... | A61K 31/277 514/235.5 |
| 2008/0102475 | A1 | 5/2008 | Kan et al. | |

(Continued)

FOREIGN PATENT DOCUMENTS

WO    WO 06/078287 A2    7/2006

OTHER PUBLICATIONS

Harada, Journal of Dermatological Science, Sep. 2008 vol. 51, Issue 3, pp. 215-219.*
Schmidt, J Allergy Clin Immunol, Oct. 2001, vol. 108, No. 4, pp. 530-536.*
Van Cauwenberge, B-ENT, 2005, 1, Suppl. 1, 45-64.*
Antoniu, "New therapeutic options in the management of COPD—focus on roflumilast," *Int. J. COPD*, 6:147-155, 2011.
Banner et al., "Dual PDE3/4 inhibitors as therapeutic agents for chronic obstructive pulmonary disease," *Br. J. Pharmacol.* 157(6):892-906, 2009.
Barber et al., "Differential expression of PDE4 cAMP phosphodiesterase isoforms in inflammatory cells of smokers with COPD, smokers without COPD, and nonsmokers," *Am. J. Physiol. Lung. Cell Mol. Physiol.* 287:322-343, 2004.

(Continued)

*Primary Examiner* — Layla D Berry
(74) *Attorney, Agent, or Firm* — Occhiuti & Rohlicek LLP

(57) ABSTRACT

The present invention is based, in part, on our studies of molecular pathways that include the deubiquitinase CYLD. Accordingly, the present invention features, inter alia, nucleic acid constructs that express CYLD or a biologically active variant thereof (e.g., a variant including the catalytic domain), nucleic acids that inhibit the expression of a negative regulator of CYLD (e.g., PDE4B or LNK2), nucleic acids that modulate the expression of downstream CYLD targets (e.g., Akt, by inhibiting or promoting the expression of the downstream target), compositions including one or more of these types of constructs (e.g., pharmaceutical compositions), kits including one or more of the compositions described herein and instructions for use, screening methods to identify therapeutic agents {e.g., anti-inflammatory agents) that upregulate CYLD, downregulate a negative regulatory of CYLD, or modulate (e.g., inhibit) a downstream CYLD target (e.g., Akt), and various methods of treatment including the administration of the nucleic acids described above, protein biotherapeutics, and/or small molecules, alone or in combination, to address cancer, inflammation, and fibrosis. The compositions described herein can be used in the preparation of a medicament (e.g., used in the preparation of a medicament to treat cancer, inflammation, fibrosis, or one or more of the more specific conditions described herein).

11 Claims, 7 Drawing Sheets

(56) References Cited

U.S. PATENT DOCUMENTS

2009/0214477 A1    8/2009  Betz et al.

OTHER PUBLICATIONS

Bender et al., "Cyclic nucleotide phosphodiesterases: molecular regulation to clinical use," *Pharmacol. Rev.* 58:488-520, 2006.

Calverley et al., "Roflumilast in symptomatic chronic obstructive pulmonary disease: two randomised clinical trials," *Lancet* 374:685-694, 2009.

Cazzola et al., "Roflumilast in chronic obstructive pulmonary disease: evidence from large trials," *Expert Opin. Pharmacother.* 11(3):441-449, 2010.

Cortijo et al., "Roflumilast, a phosphodiesterase 4 inhibitor, alleviates bleomycin-induced lung injury," *Br. J. Pharmacol.* 156:534-544, 2009.

Fabbri et al., "Roflumilast in moderate-to-severe chronic obstructive pulmonary disease treated with long acting bronchodilators: two randomised clinical trials," *Lancet* 374:695-703, 2009.

Field, "Roflumilast, a novel phosphodiesterase 4 inhibitor, for COPD patients with a history of exacerbations," *Clin. Med. Insights Circ. Respir. Plum. Med.* 5:57-50, 2011.

Giembycz et al., "Roflumilast first phosphodiesterase 4 inhibitor approved for treatment of COPD," *Drug Des. Devel. Ther.* 4:147-158, 2010.

Herve et al., "The PDE4 inhibitor Rolipram prevents NF-κB binding activity and proinflammatory cytokine release in human chorionic cells," *J. Immunol.* 181(3):2196-2202, 2008.

Jin et al., "Induction of the cyclic nucleotide phosphodiesterase PDE4B is essential for LPS-activated TNF-α responses," *Proc. Natl. Acad. Sci. U.S.A.* 99(11):7628-7633, 2002.

Johnson et al., "An evolutionary analysis of cAMP-specific phosphodiesterase 4 alternative splicing," *BMC Evol. Biol.* 10:247, 2010.

Kodimuthali et al., "Recent advances on phosphodiesterase 4 inhibitors for the treatment of asthma and chronic obstructive Pulmonary Disease," *J. Med. Chem.* 51(18):5471-5489, 2008.

Kwak et al., "Roflumilast inhibits lipopolysaccharide-induced inflammatory mediators via suppression of nuclear factor-κB, p38 mitogen-activated protein kinase, and c-Jun NH2-terminal kinase activation," *J. Pharmacol. Exp. Ther.* 315:1188-1195, 2005.

Lee et al., "Inhibition of c-Jun $NH_2$-terminal kinase or extracellular signal-regulated kinase improves lung injury," *Respir. Res.* 5(23):1-15, 2004.

Lipworth, "Phosphodiesterase-4 inhibitors for asthma and chronic obstructive pulmonary disease," *Lancet* 365:167-175, 2005.

Lugnier, "Cyclic nucleotide phosphodiesterase (PDE) superfamily: a new target for the development of specific therapeutic agents," *Pharmacol. Ther.* 106:366-398, 2006.

Manallack et al., "The next generation of phosphodiesterase inhibitors: structural clues to ligand and substrate selectivity of phosphodiesterases," *J. Med. Chem.* 48(10):3449-3462, 2005.

O'Byrne et al., "Phosphodiesterase-4 inhibition in COPD," *Lancet* 374(9691):665-667, 2009.

Omori et al., "Overview of PDEs and their regulation," *Circ. Res.* 100:309-327, 2007.

Page et al., "Phosphodiesterase inhibitors in the treatment of inflammatory diseases," *Handb. Exp. Pharmacol.* 204:391-414, 2011.

Page et al., "Selective PDE inhibitors as novel treatments for respiratory diseases," *Curr. Opin. Pharmacol.* 12(3):275-286, 2012.

Raderer et al., "Inhibition of histamine liberation in allergic rhinoconjunctivitis in relation to the season," *Wien. Med. Wochenschr.* 145(17-18):456-458, 1995.

Smith et al., "Selective phosphodiesterase 4 inhibitors in the treatment of allergy and inflammation," *Curr. Opin. Investig. Drugs* 6(11):1136-1141, 2005.

Spina, "Phosphodiesterase-4 inhibitors in the treatment of inflammatory lung disease," *Drugs* 63(23):2575-2594, 2003.

Spina, "PDE4 inhibitors: current status," *Br. J. Pharmacol.* 155:308-315, 2008.

Visser et al., "Phosphodiesterase-4 inhibition attenuates pulmonary inflammation in neonatal lung injury," *Eur. Respir. J.* 31:633-644, 2008.

Wang et al., "Evaluation of PDE4 inhibition for COPD," *Int. J. COPD* 1(4):373-379, 2006.

\* cited by examiner

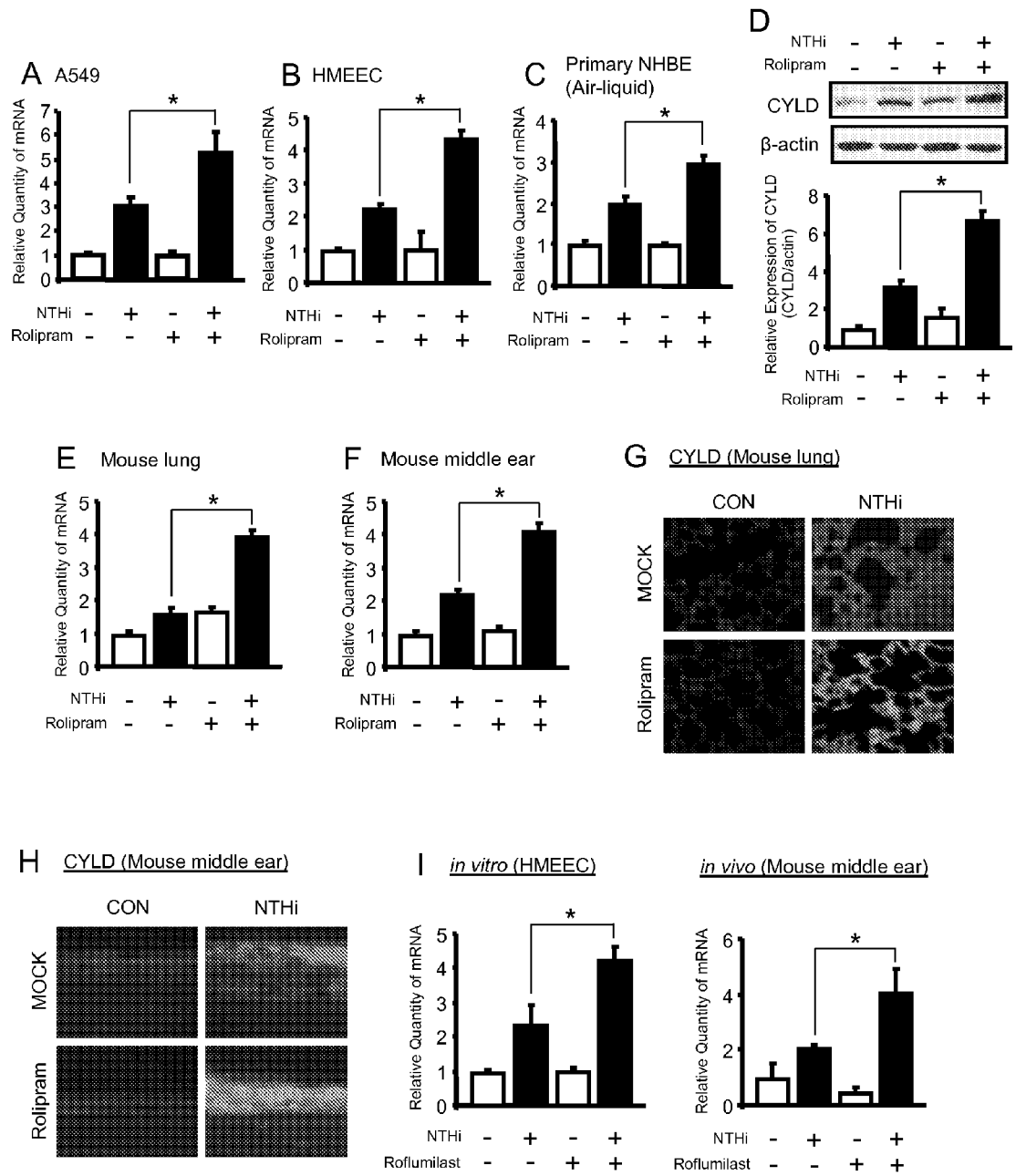
Figure 1. PDE4 Acts as a Key Negative Regulator for NTHi-induced Up-regulation of CYLD Expression

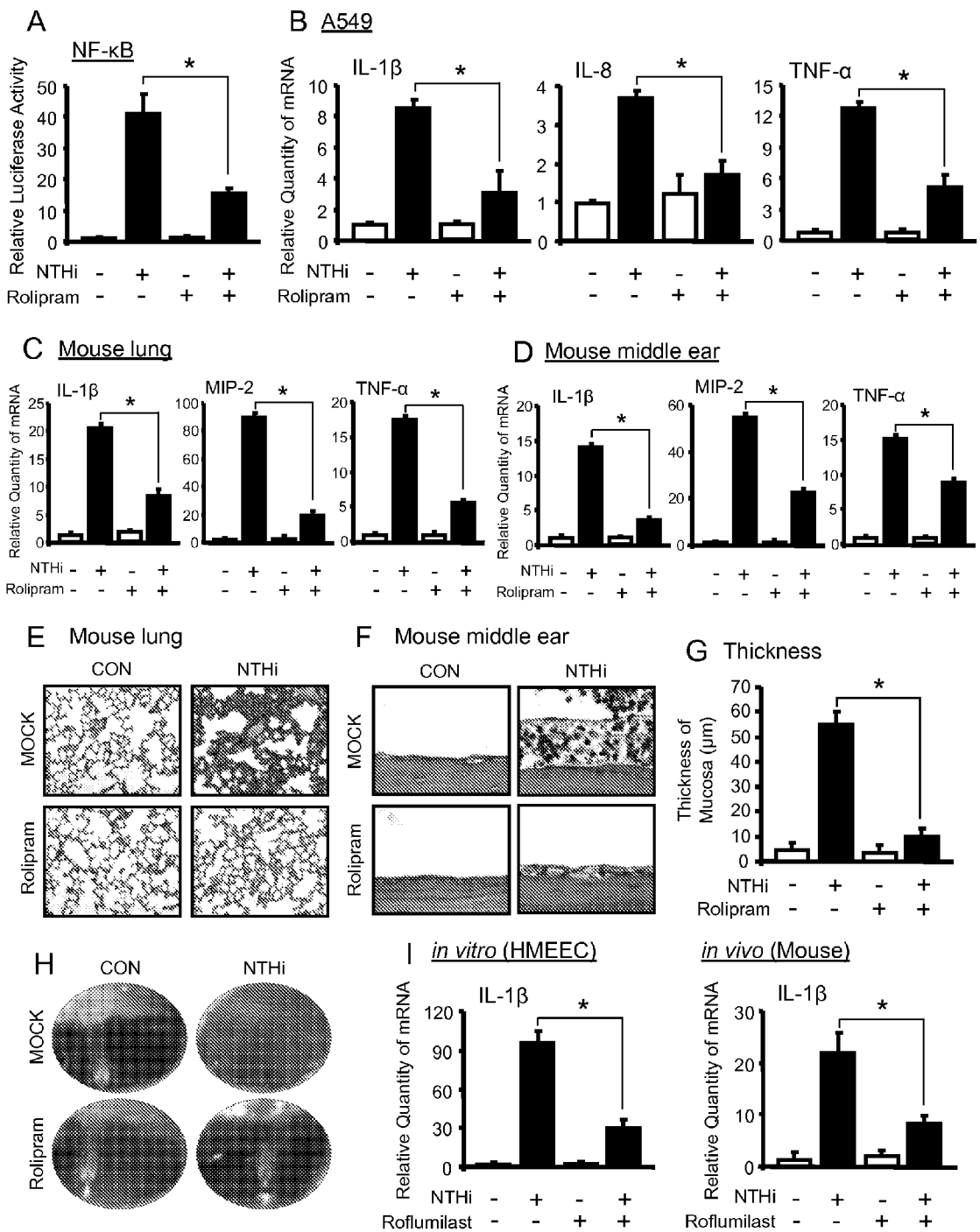
Figure 2. Inhibition of PDE4 Leads to Suppression of NTHi-induced Inflammation *in vitro* and *in vivo*

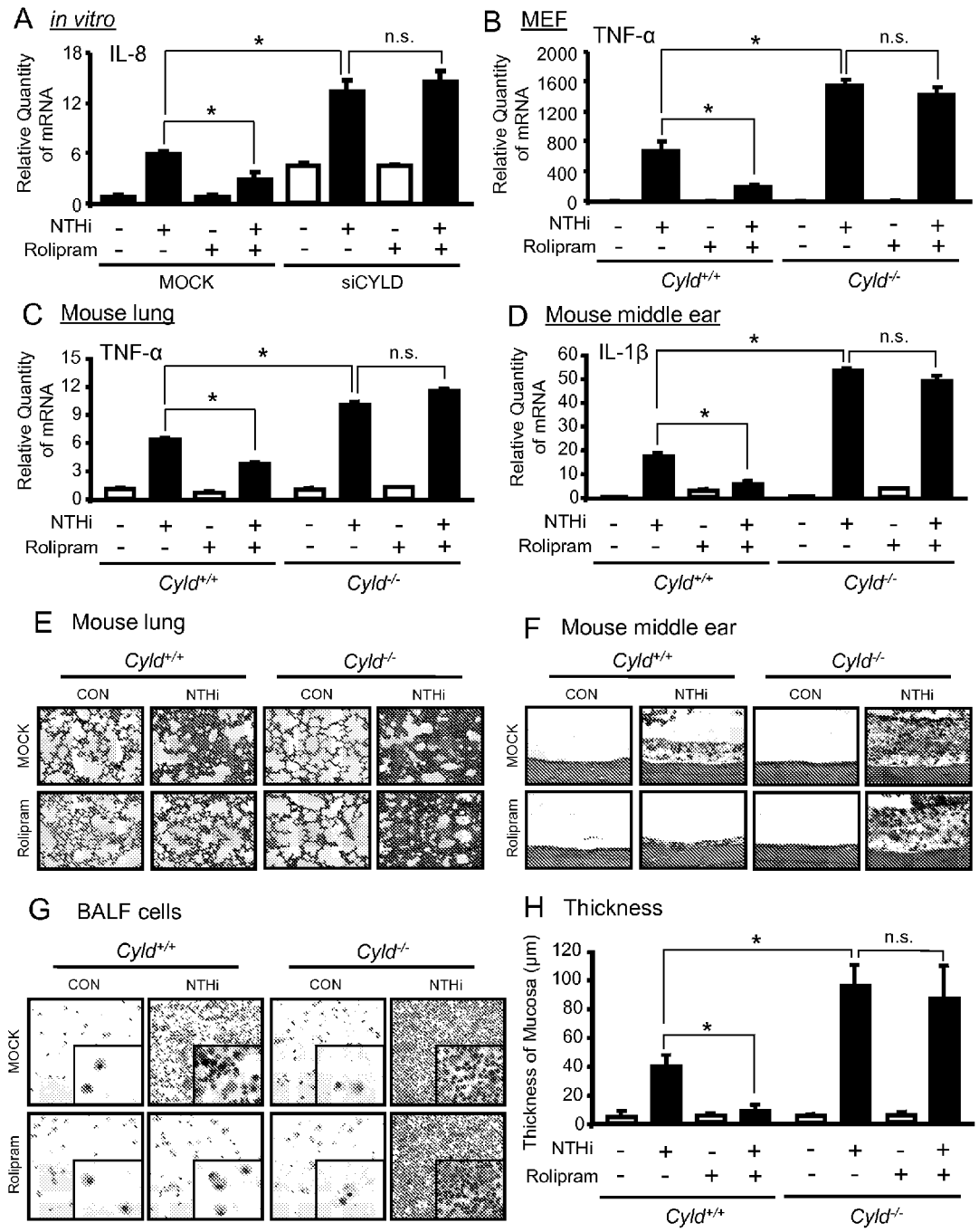
Figure 3. Inhibition of PDE4 Leads to Suppression of NTHi-induced Inflammation via Up-regulating CYLD Expression *in vitro* and *in vivo*

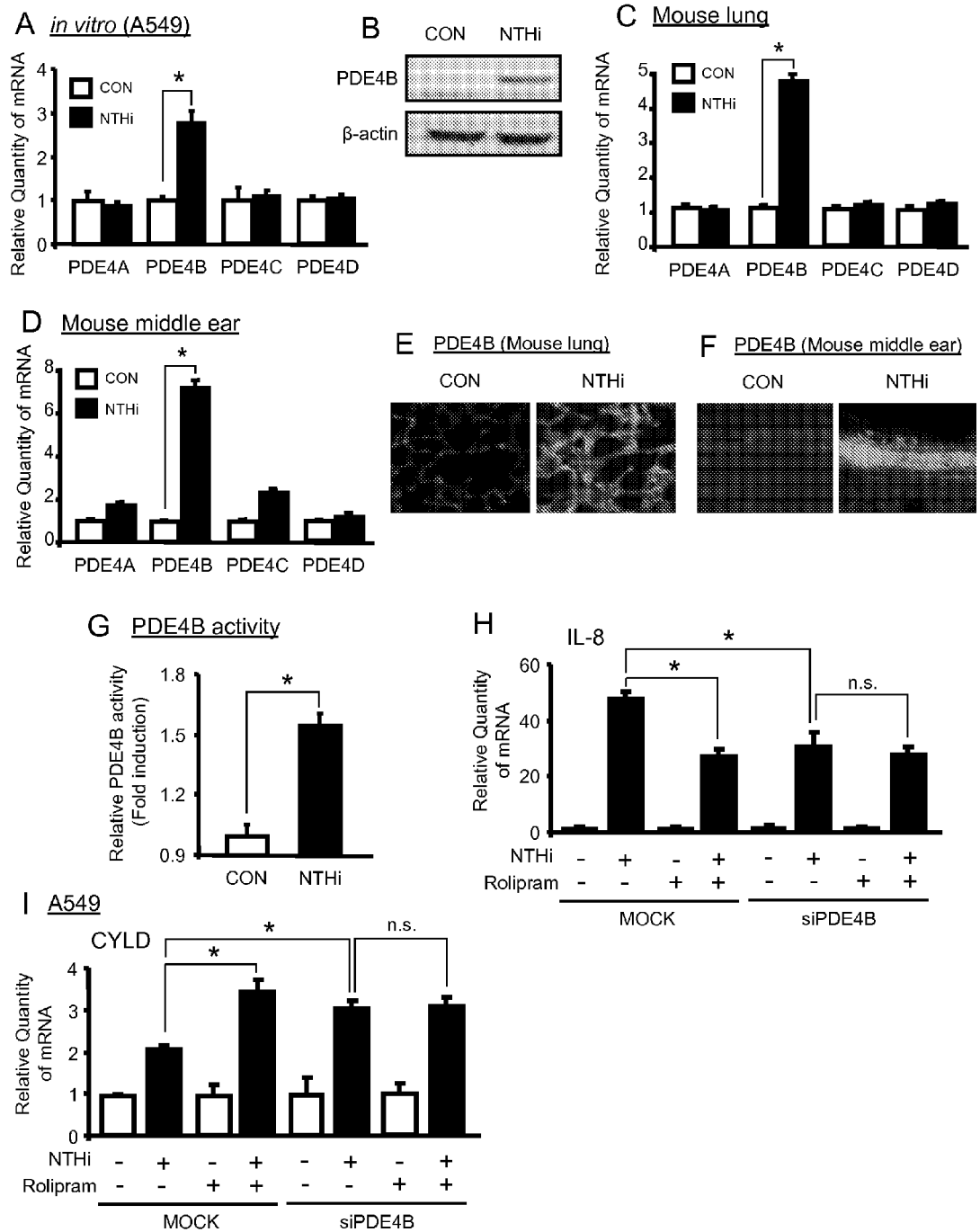
Figure 4. PDE4B Plays a Crucial Role in Mediating NTHi-induced Inflammation by Negatively Regulating CYLD Expression

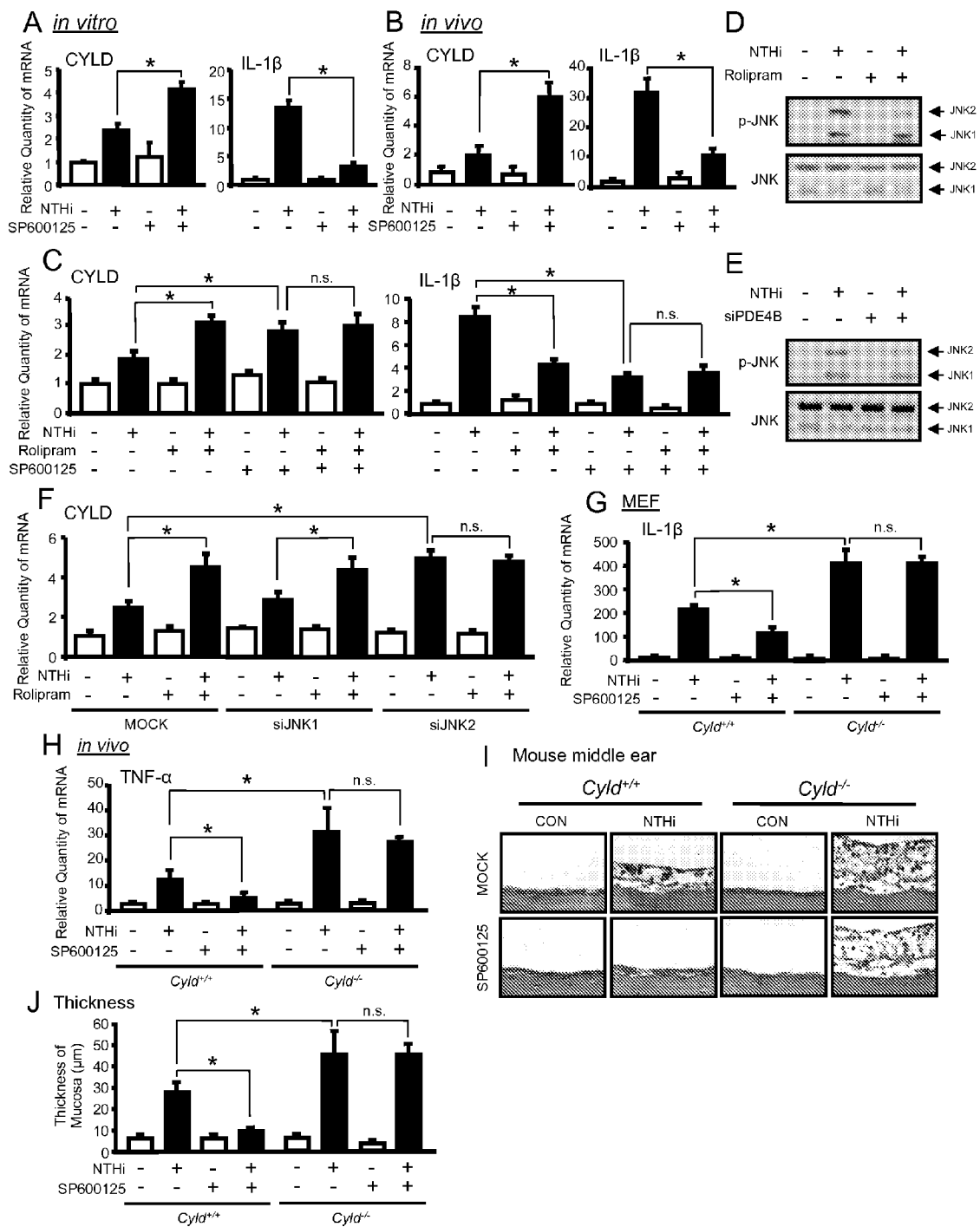
Figure 5. PDE4B Negatively Regulates CYLD Expression and Mediated Inflammation by NTHi via JNK2 but not JNK1 Pathway

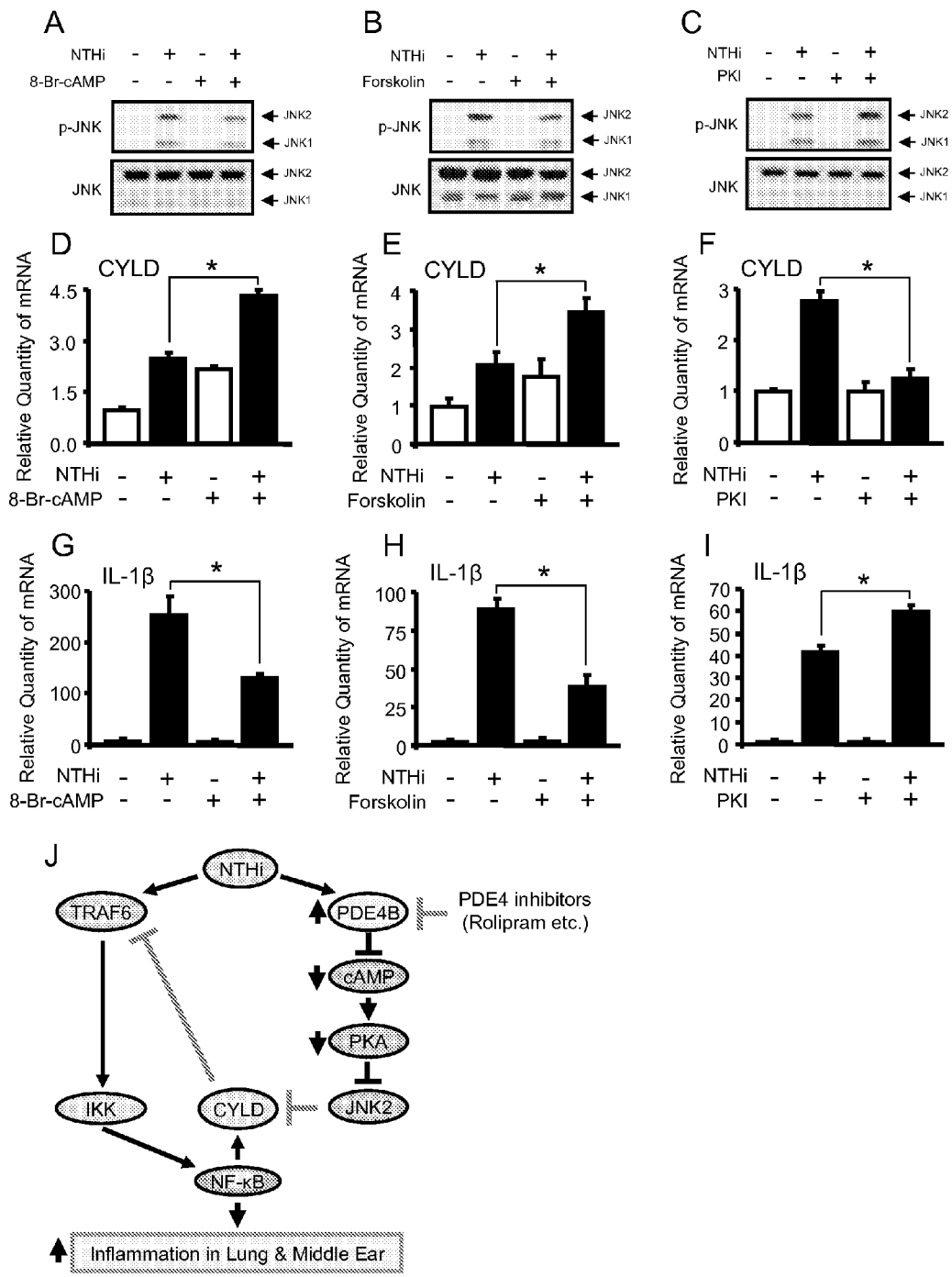
Figure 6. PDE4B Mediates NTHi-induced Activation of JNK2 via Inhibition of cAMP-PKA-dependent Pathway, which in turn Leads to Suppression of CYLD and Subsequent Induction of Inflammation

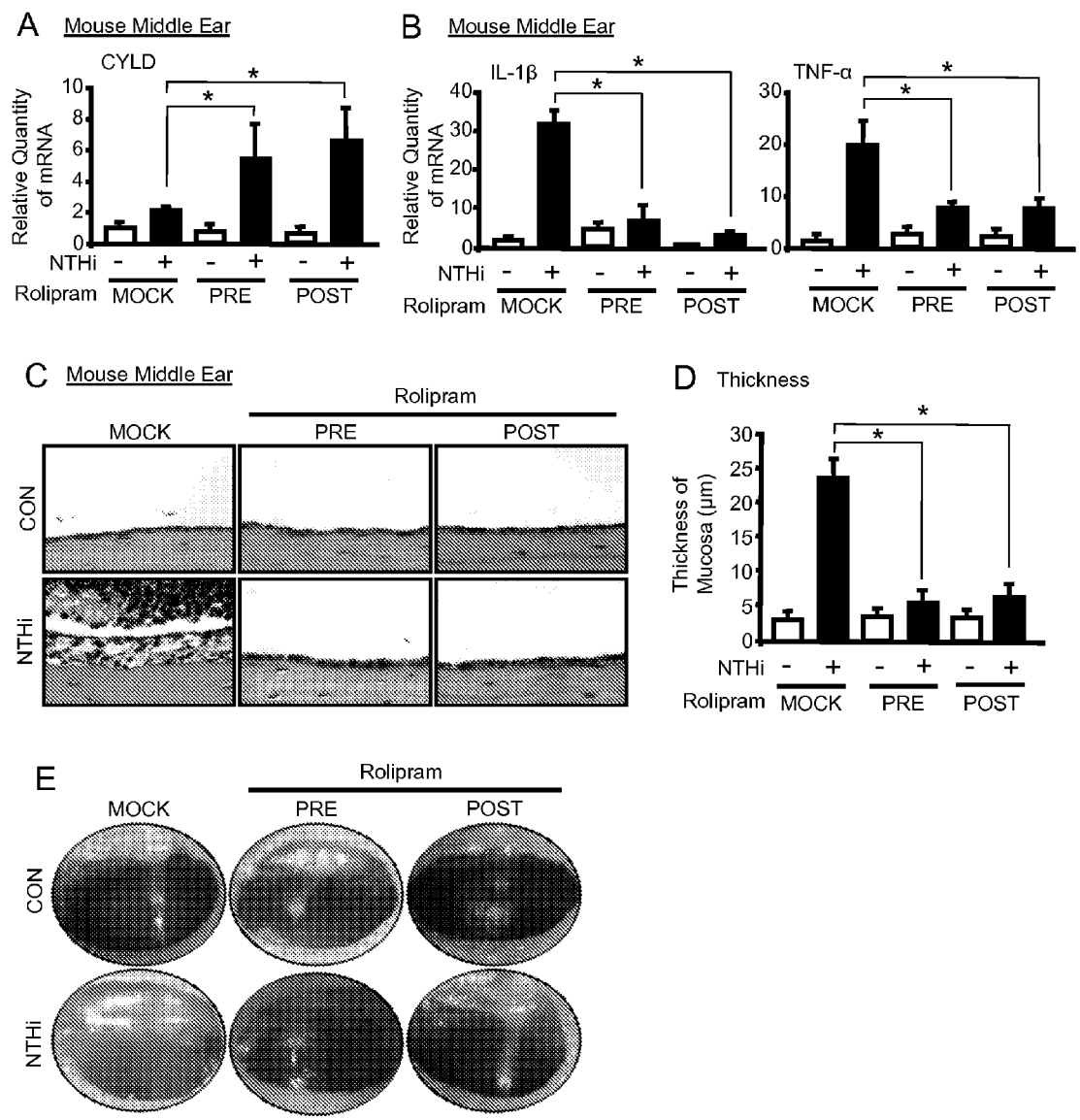
Figure 7. Ototopical Pre- and Post-inoculation Administration of Specific PDE4 inhibitors Up-regulated CYLD and Suppressed Inflammation in a Well-established Mouse OM Model

COMPOSITIONS AND METHODS FOR TREATING OTITIS MEDIA AND OTHER CONDITIONS WITH INHIBITORS OF CYLD

CROSS-REFERENCE TO RELATED APPLICATIONS

This application is a U.S. national phase application of the international application PCT/US2013/035863, filed Apr. 9, 2013, which claims the benefit of the filing date of U.S. Provisional Application No. 61/622,486, which was filed Apr. 10, 2012. The content of the earlier-filed provisional application is hereby incorporated by reference herein in its entirety.

STATEMENT REGARDING FEDERALLY SPONSORED RESEARCH

This invention was made with government support under Grant Number DC005843 awarded by the National Institutes of Health. The government has certain rights in the invention.

FIELD OF THE INVENTION

The invention is generally directed to methods for treating or preventing a medical condition by modulating an inflammatory response in a subject, such as that caused in response to a pathogen or chemical irritant. More particularly, in one aspect, the invention is directed to compositions and methods for upregulating the expression of the gene encoding the deubiquitinase CYLD (cylindromatosis) or the activity of the encoded enzyme. In other aspects, the invention features compositions and methods of modulating other cellular components that affect or that are affected by CYLD. The compositions can include two active agents, as described further below.

BACKGROUND OF THE INVENTION

Inflammation is the complex biological response of tissues to harmful stimuli, such as pathogens, damaged cells, or irritants, as well as to mechanical trauma, toxins, and neoplasia. Inflammation occurs as a defensive response to invasion of the host by foreign material and is classified as either acute or chronic. Acute inflammation is the initial response of the body to harmful stimuli and is achieved by the increased movement of plasma and leukocytes from the blood into the injured tissues. A cascade of biochemical events propagates and matures the inflammatory response, involving the local vascular system, the immune system, and various cells within the injured tissue. Chronic (prolonged) inflammation leads to a progressive shift in the type of cells that are present at the site of inflammation and is characterized by simultaneous destruction and healing of the tissue from the inflammatory process.

Excessive inflammation or prolongation of the inflammatory process may lead to local tissue damage, to post-infectious syndromes such as in fibrotic lesions and to rheumatic diseases such as systemic lupus erythematosus and rheumatoid arthritis, or even to inflammatory response-induced diseases as diverse as diabetes, arteriosclerosis, cataracts, reperfusion injury, and cancer.

SUMMARY

The present invention is based, in part, on our studies of molecular pathways that include the deubiquitinase CYLD. Accordingly, the present invention features, inter alia, nucleic acid constructs that express CYLD or a biologically active variant thereof (e.g., a variant including the catalytic domain), nucleic acids that inhibit the expression of a negative regulator of CYLD (e.g., PDE4B or JNK2), nucleic acids that modulate the expression of downstream CYLD targets (e.g., Akt, by inhibiting or promoting the expression of the downstream target), compositions including one or more of these types of constructs (e.g., pharmaceutical compositions), kits including one or more of the compositions described herein and instructions for use, screening methods to identify therapeutic agents (e.g., anti-inflammatory agents) that upregulate CYLD, downregulate a negative regulator of CYLD, or modulate (e.g., inhibit) a downstream CYLD target (e.g., Akt), and various methods of treatment. Instead of, or in addition to, a nucleic acid as described above, the compositions can include, and the present methods of treatment can be carried out with, a protein biotherapeutic or small molecule that enhances the expression or activity of CYLD, inhibits the activity of a negative regulator of CYLD, or modulates (e.g., suppresses) the activity of a downstream CYLD target (e.g., Akt). Where the therapeutic agent is targeted to PDE4B, the therapeutic agent can be one that selectively inhibits the expression or activity of a PDE4B isoform (as opposed to non-selective inhibition of a PDE4B isoform relative to, for example, another phosophodiesterase such as PDE4A, PDE4C, or PDE4D isoform). We use the terms "therapeutic agent" and "pharmaceutical agent" interchangeably.

More specifically, the invention features compositions including a single active agent as well as compositions including two or more active agents. While suitable formulations are described further below, we note here that the compositions can be formulated as pharmaceutical compositions or stock solutions in which any active therapeutic agents are too concentrated or otherwise unsuitable for administration to a patient. For example, the invention features compositions including, as either a single active pharmaceutical agent or as the first of a plurality of active pharmaceutical agents, a nucleic acid construct of the invention (e.g., a nucleic acid construct from which CYLD is expressed; from which or by which PDE4B is inhibited; or from which or by which Akt is modulated (e.g., expressed or inhibited)). The field of molecular biology is now well advanced, and one of ordinary skill in the art will be familiar with a wide variety of expression vectors and systems that can be employed to achieve the outcomes described herein. The nucleic acid constructs from which CYLD can be expressed, for example, can be fashioned from any number of plasmids or viral vectors. Nucleic acid constructs for suppressing gene expression are also now well known, with such nucleic acids including antisense oligonucleotides, microRNAs, and nucleic acids that mediate RNAi (e.g., siRNAs and shRNAs). See, for example, U.S. Pat. No. 8,415,526, entitled "Down-regulation of gene expression using artificial microRNAs." The compositions can also include, as either a single active pharmaceutical agent or as the first of a plurality of active pharmaceutical agents, a protein therapeutic, such as an antibody, that inhibits PDE4B or Akt, or a small molecule (a chemical compound) that promotes the activity of CYLD, inhibits PDE4B, or modulates Akt. The second active agent can be, for example, an anti-inflammatory agent that is also a nucleic acid, protein therapeutic, or a small molecule. The second agent can be, for example, a steroid (e.g., dexamethasone), a non-steroidal anti-inflammatory drug (e.g., aspirin, ibuprofen, or naproxen), an immune-selective anti-inflammatory derivative (e.g., the 7-mer SGP-T or the 3-mer FEG), vinpocetine, rolipram, roflumilast, cilomilast, Ro 20-1724, or a compound as described in WO 2007/142929. Other combination therapeutics include two or more of: a steroid (e.g., dexamethasone), a non-steroidal anti-inflammatory drug (e.g., aspirin, ibuprofen, or naproxen), an immune-selective anti-inflammatory derivative (e.g., the 7-mer SGP-T or the 3-mer FEG), vinpocetine, rolipram, roflumilast, cilomilast, Ro 20-1724, or a compound as described in WO 2007/142929. For example, in one embodiment, the invention features a composition (e.g., a pharmaceutical composition) including dexamethasone and vinpocetine.

The foregoing agents, whether administered alone, combined in a single formulation, or simply administered by way of separate formulations to the same patient, can be used in the methods described herein to treat patients suffering from a wide variety of conditions, including conditions in which inflammation is believed to play a causative role or in which inflammation is a common sign. Thus, the invention features methods including a step of administering, to a patient in need, a therapeutically effective amount of a pharmaceutical composition described herein. The sole or first active agent can be, as described above, a nucleic acid construct, a protein biotherapeutic, or a small molecule. When included, the second active agent can be, for example, an anti-inflammatory agent that is also a nucleic acid or that, in other embodiments, is a small molecule such as a steroid (e.g., dexamethasone), a non-steroidal anti-inflammatory drug (e.g., aspirin, ibuprofen, or naproxen), an immune-selective anti-inflammatory derivative (e.g., the 7-mer SGP-T or the 3-mer FEG), vinpocetine, rolipram, roflumilast, cilomilast, Ro 20-1724 or a compound as described in WO 2007/142929. Other combination therapeutics that can be administered to treat a condition as described herein include two or more of: a steroid (e.g., dexamethasone), a non-steroidal anti-inflammatory drug (e.g., aspirin, ibuprofen, or naproxen), an immune-selective anti-inflammatory derivative (e.g., the 7-mer SGP-T or the 3-mer FEG), vinpocetine, rolipram, roflumilast, cilomilast, Ro 20-1724, or a compound as described in WO 2007/142929.

The compositions described herein can be used in the preparation of a medicament (e.g., used in the preparation of a medicament to treat cancer, inflammation, fibrosis, or any one or more of the conditions described more specifically herein). Thus, another embodiment of the invention includes a use of a composition as described herein in the manufacture of a medicament for use in treating a condition described herein.

Treatable conditions include cancer, inflammation, and fibrosis, which may affect many different organs or organ systems. In particular embodiments, the condition treated with a composition as described herein can be associated with inflammation of, or mucus overproduction in, the ears (either or both), the nose, or the throat, and may also affect the nasal passages, another area or tissue within the respiratory system (e.g., the lungs or bronchial tree), or a sinus cavity or passage extending from such a cavity. For example, the condition can be an interstitial lung disease, human fibrotic lung disease (e.g., idiopathic pulmonary fibrosis (IPF), cystic fibrosis, respiratory distress syndrome (adult (ARDS) or infant), tumor stroma in lung disease, systemic sclerosis, Hermansky-Pudlak syndrome (HPS), coal worker's pneumoconiosis (CWP), chronic pulmonary hypertension, AIDS-associated pulmonary hypertension, and the like, asthma, chronic bronchitis, chronic obstructive pulmonary disease (COPD), cough (e.g., eosinophilic cough), pulmonary fibrosis, rhinitis (e.g., allergic rhinitis), sinusitis, or otitis media. In other embodiments, the condition treated with a composition as described herein can be a human kidney disease. For example, a patient may have nephrotic syndrome, Alport's syndrome, HIV-associated nephropathy, polycystic kidney disease, Fabry's disease, a diabetic or other nephropathy, glomerular nephritis (e.g., chronic glomerulonephritis) or nephritis associated with systemic lupus. As noted, the present compositions can be effective against fibrosis, including fibrotic conditions in the liver (liver fibrosis), heart (myocardial fibrosis), and reproductive system (endometrial fibrosis). Where the liver is concerned, treatable conditions also include hepatitis (whether caused by a viral agent, autoimmune disease, or substance abuse), hepatic steatosis, and hepatic cirrhosis. In other embodiments, the condition treated with a composition as described herein can be a cardiovascular disease, including arterial restenosis and atherosclerosis, or a reperfusion injury of the myocardium. In other embodiments, the condition treated with a composition as described herein can be a cancer, and the present compositions can be used to impede tumor growth and/or metastasis. Particular cancers amenable to treatment include scleroderma, glioblastoma in Li-Fraumeni syndrome, sporadic glioblastoma, myeloid leukemia, acute myelogenous leukemia, myelodysplastic syndrome, myeloproliferative syndrome, cancers such as breast cancer, lung cancer, colon cancer (e.g., Lynch syndrome), prostate cancer or a gynecological cancer (e.g., ovarian or uterine cancer), and skin cancer (e.g., a melanoma or Kaposi's sarcoma). In addition to skin cancers or malignant proliferative skin diseases, the compositions of the invention can be used to treat eosinophilic granulomas, other benign skin diseases such as atopic dermatitis (a type of eczema) and urticaria (commonly known as hives), and scarring. In another embodiment, the present compositions and methods can be applied to a patient exhibiting metaplasia, which is generally understood to be a benign change that occurs in response to changes in milieu or chronic irritation. For example, cells and tissue within a patient's airway can exhibit metaplasia in response to smoke (e.g., smoke that is inhaled from a tobacco product such as a cigar or cigarette). While the invention is not so limited, in this instance, the irritant can cause the mucus-secreting ciliated pseudostratified columnar respiratory epithelial cells that line the airways to be replaced by stratified squamous epithelium. As noted, the present compositions can be effective against inflammatory conditions, including those that affect the gastrointestinal tract. These include inflammatory bowel disease (e.g., ulcerative colitis or Crohn's disease), and the present compositions are also useful in treating hypersecretion of gastric acid. In other embodiments, the condition treated with a composition as described herein can be a neurological disorder or an injury to the nervous system (e.g., the peripheral or central nervous system). For example, the condition can be a reperfusion injury of the brain, depression, memory impairment, monopolar depression, Parkinson's disease, Alzheimer's disease, Huntingtin's disease, spinal cord trauma, head injury, neurogenic inflammation, or pain. There is increasing evidence that neurodegenerative disorders and injuries have important inflammatory components, and any such disorders or injuries can be treated with the compositions described herein. In other embodiments, the condition treated with a composition as described herein can be an autoimmune disorder such as multiple sclerosis, rheumatoid arthritis, Grave's ophthalmopathy, psoriasis, or diabetes insipidus. Transplant rejection and graft versus host disease can also be treated. In other embodiments, the condition treated with a composition as described herein can be an infectious disease associated with a bacterial or viral pathogen. For example, the condition can be an infectious disease caused by a bacterium of the genus *Streptococcus* (e.g., *S. pneumoniae*, sometimes called *pneumococcus* or *S. pyogenes*), by nontypable *Haemophilus influenzae* (NTHi), or by *Pseudomas aeruginosa*. Other treatable infectious diseases are associated with a virus (e.g., a respiratory syncytial virus or an influenza virus). Hansen's disease, bacterial, fungal or viral induced sepsis or septic shock (endotoxic shock) can also be treated. In other embodiments, the condition treated with a composition as described herein can affect a reproductive or genitourinary tissue or organ. For example, the patient can be one who is suffering from a medical condition associated with inflammation of a reproductive organ (e.g., prostatitis, pelvic inflammatory disease, or an infectious disease that causes inflammation of a reproductive tissue or organ). In other embodiments, the condition treated with a composition as described herein can affect the skeletomuscular system. For example, a patient may be suffering from inflammatory arthritis, osteoarthritis, osteoporosis, inflammation and cytokine-mediated chronic tissue degeneration, muscle wasting, cachexia, or ankylosing spondylitis. In other embodiments, the condition treated with a composition as described herein can be drug induced ergotism, allergic conjunctivitis, vernal conjunctivitis, obesity, or pancreatitis.

Any of the methods of the invention that concern a therapeutic or prophylactic treatment can include a step of identifying a patient in need of treatment (e.g., by performing a diagnostic test or assay). For example, a physician or other healthcare provider can identify a patient showing signs of inflammation such as an increased temperature, redness, swelling, and loss of function (e.g., in a tissue, organ, or system as described herein). The patient may also complain of pain or stiffness. Where the condition involves abnormal cellular proliferation, a physician or other healthcare provider can similarly assess the patient with appropriate diagnostic tools (e.g., cancer biomarkers and imaging agents). As the invention encompasses veterinary applications, the patient can be a human or another mammal, such as a domesticated pet (e.g., a cat or dog), livestock, a horse, or animals kept in captivity (e.g., in a zoo). We may use the terms "patient" and "subject" interchangeably. The methods described herein are applicable to subjects of any age. For example, where the patient is a human, the human can be an infant or child.

In one embodiment, the invention features methods of treating a patient who is suffering from a medical condition associated with inflammation of, or mucus overproduction in, the ears (either or both (e.g., otitis media)), nose, nasal passages, another tissue or organ within the respiratory system (e.g., the lungs or bronchial tree) a sinus cavity or passage extending from such a cavity, the oral cavity and/or throat. Thus, the condition can be defined as one associated with either the lower and/or the upper respiratory tract. The methods can be carried out by administering to the patient a therapeutically effective amount of a pharmaceutical composition described herein. By "effective amount" we mean an amount of the therapeutic or pharmaceutical agent that elicits a clinically beneficial response. As described above, the methods encompass the treatment of a wide variety of subjects, including infants and children. The agent that downregulates the expression of the Akt gene can be a nucleic acid that inhibits the Akt gene (e.g., an antisense oligonucleotide, a microRNA, or a nucleic acid that mediates RNAi). In one embodiment, the agent that inhibits the activity of the encoded kinase can be a nucleic acid construct that expresses an enzyme that deubiquitinates Akt (e.g., the enzyme CYLD). In another embodiment, the agent that inhibits the activity of the encoded kinase can be VQD-002, perifosine, or miltefosine. As noted, the pharmaceutical composition can be formulated for ototopic or nasal administration.

The agent that upregulates the expression of CYLD can be an inhibitor of phosphodiesterase 4 (PDE4 (e.g., PDE4B)) or an inhibitor of c-jun N-terminal kinase 2 (JNK2). In any event (i.e., in any aspect or embodiment of the invention), the inhibitor of PDE4 can be specific for PDE4B. For example, the inhibitor can be one that inhibits PDE4B but does not significantly inhibit PDE4D. To selectively inhibit PDE4B, one can administer a nucleic acid (e.g., a nucleic acid construct) that inhibits PDE4B gene expression. Such nucleic acids are known in the art and include antisense oligonucleotides, microRNAs, and nucleic acids that mediate RNAi (e.g., siRNAs and shRNAs). Useful chemical inhibitors of PDE4 include rolipram, roflumilast, and cilomilast. Other useful inhibitors are those described in WO 2007/142929 (the entire content of which is incorporated by reference herein). These inhibitors include a substituted benzene or substituted six-membered heteroaryl rings comprising one or two ring nitrogens, the substitution comprising an ether, thioether, or amine group in which the alkyl group on the ether, thioether, or amine is a haloalkyl group. The haloalkyl group can be a fluoromethyl, difluoromethyl, or trifluoromethyl group.

The agent that upregulates the expression of CYLD is an inhibitor of JNK2. For example, the inhibitor of JNK2 can be a JNK interacting protein (JIP) or a peptide fragment thereof, optionally linked to the cell-penetrating peptide TAT (as described, for example, in Kaoud et al. (*ACS Chem. Biol.* 6:658-666, 2011)) or a 2,4-diaminopyrimidine (as described, for example, in Song et al. (*Med. Chem. Commun* 3:238-243, 2012)). The inhibitor of JNK2 can also be a nucleic acid that inhibits JNK2 gene expression. Wherever one wishes to inhibit a target with a nucleic acid construct, whether JNK2 or another target described herein, one can use antisense oligonucleotides, microRNAs, or nucleic acids that mediate RNAi (e.g., siRNAs and shRNAs).

In any of the methods requiring a pharmaceutical composition for treatment of a condition affecting the ears or nose, the composition can be formulated for ototopic or nasal administration.

In another embodiment, the invention features methods of treating a patient who is suffering from a medical condition associated with inflammation of a reproductive organ (e.g., prostatitis, pelvic inflammatory disease, or an infectious disease that causes inflammation of a reproductive tissue or organ). The methods can be carried out by administering to the patient a therapeutically effective amount of a pharmaceutical composition comprising an agent that upregulates the expression of the gene cylindromatosis (CYLD) or the activity of the encoded deubiquitinase. The agents can be those described above. Alternatively, or in addition, this patient population can also be treated with a therapeutically effective amount of a pharmaceutical composition comprising an agent that downregulates the expression of the Akt gene or inhibits the activity of the encoded kinase.

In another embodiment, the invention features methods of treating a patient who is suffering from an autoimmune disease, particularly psoriasis or rheumatoid arthritis. The methods comprise administering to the patient a therapeutically effective amount of a pharmaceutical composition comprising an agent that upregulates the expression of the gene cylindromatosis (CYLD) or the activity of the encoded deubiquitinase. In these methods, any of the agents described above or elsewhere herein can be formulated for administration. As psoriasis affects the skin, the formulations intended for treatment of that condition can be topical. Further, and as noted, these methods can be carried out using an inhibitor of PDE4 that inhibits PDE4B but does not significantly inhibit another PDE4-family member (e.g., PDE4D). These selective inhibitors can be nucleic acids (e.g., a nucleic acid construct) designed using methods known in the art to generate sequence-specific targeting molecules (e.g., antisense oligonucleotides, microRNAs, and nucleic acids that mediate RNAi (e.g., siRNAs and shRNAs)). In another embodiment, the agent that upregulates the expression of CYLD can be an inhibitor of JNK2.

In another embodiment, the invention features methods of treating a patient who is suffering from an autoimmune disease, particularly psoriasis or rheumatoid arthritis by administering to the patient a therapeutically effective amount of a pharmaceutical composition comprising an agent that downregulates the expression of the Akt gene or inhibits the activity of the encoded kinase.

In another embodiment, the invention features methods of treating a wide variety of conditions by administering a selective inhibitor of PDE4B (e.g., a nucleic acid that, through sequence-specific interaction, specifically inhibits the expression of PDE4B or a compound therapeutic). In some embodiments, a treatable condition as described herein can be present acutely, and the compositions and methods described herein can be acutely applied (e.g., over a period most conveniently measured in days or weeks). In other embodiments, the condition can be chronic, and the compositions and methods described herein can be applied chronically (e.g., over a period most conveniently measured in months or years).

In another embodiment, the invention features methods of identifying a therapeutic agent. The methods can be carried out by including the steps of: (a) providing a test agent; (b) exposing the agent to PDE4B and, concurrently or separately, to another PDE (e.g., PDE4D); and (c) assaying the level of expression of the genes encoding PDE4B and the other PDE (e.g., PDE4D) and/or the level of activity of the encoded phosphodiesterases. An agent that inhibits the expression or activity of PDE4B but does not significantly inhibit the expression or activity of the other PDE assayed (e.g., PDE4D) is a potential therapeutic agent for the treatment of cancer, inflammation, or fibrosis and, more particularly, for any of the patient populations referenced herein (e.g. patients with otitis media or other inflammatory-related conditions affecting the ear, nose, throat, or respiratory system).

We refer herein to biologically active variants of a given agent. For example, nucleic acid constructs of the invention (e.g., constructs encoding a CYLD) can include a sequence that is a biologically active variant of a naturally occurring gene. These variants can differ from their naturally occurring counterparts by virtue of a deletion, addition, or substitution of one or more nucleotides. Thus, the biologically active variant of the gene encoding CYLD can be a fragment thereof that encodes, for example, the catalytic domain, or can be a substitution mutant. Substitution mutants may vary at the third position within a codon, encoding the same amino acid residue as an unaltered sequence, and the sequences may be codon optimized. Similarly, where the agent is a polypeptide, the sequence of a biologically active variant may be shorter, longer, or otherwise different (e.g., by virtue of a substitution of one or more amino acid residues) from its naturally occurring counterpart. An agent is biologically active when it is useful in the present compositions and methods. It need not be identical in all, or even most, respects to a natural counterpart. For ease of reading, we do not repeat the phrase "or a biologically active variant thereof" at every opportunity. It is to be understood that where a naturally occurring agent is useful as described herein, a biologically active variant thereof is useful as well.

BRIEF DESCRIPTION OF THE DRAWINGS

FIG. 1 illustrates CYLD as a negative regulator for lung fibrosis in the mouse and human.

FIG. 1a is a panel of photomicrographs showing H&E and Masson's trichrome (Trichrome) staining of lung tissues from Cyld+/+ and Cyld−/− mice 2-weeks post S. pneumoniae infection (insert: ×400). Scale bars correspond to 200 μm. FIG. 1b is a bar graph illustrating the relative quantity of mRNA expression of type I and type III collagens (COL1A2 and COL3A1), CTGF and type 1 plasminogen activator inhibitor (PAI-1) compared with an internal control. Glyceraldehyde 3-phosphate dehydrogenase was measured in the lung tissues of Cyld+/+ and Cyld−/− mice 2-weeks post S. pneumoniae infection. * $P<0.05$ values are the means±s.d. (n=3). Un-paired Student's t-test was used for comparison with Cyld+/+. FIG. 1c is a panel of photomicrographs of H&E, Masson's trichrome, and anti-CYLD staining of control (Con) and lung fibrosis tissues of human patients (Fibrotic lung). Lung fibrosis tissues were obtained from the patients with pulmonary fibrosis, during pneumonectomy, and normal control tissues were obtained from the patient with pneumothorax during the surgery. Slides are representative of 5 (Con) and 10 (Fibrotic) human lung tissues. Scale bars, 200 μm.

FIG. 2 illustrates that CYLD prevents development of lung fibrosis via inhibition of TGF-β-signalling. In the immunoblots of FIG. 2a, epithelial cells transfected with siRNA-Control (siCon) or siCYLD were analysed by immunoblotting with the indicated antibodies. FIG. 2b is a bar graph in which NF-κB-promoter activity is shown in siCon- or siCYLD-transfected cells stimulated with TNF-α (10 ng ml$^{-1}$). FIG. 2c is a pair of bar graphs illustrating SBE-promoter and PAI-1-promoter activity in siRNA-control (siCon) or siCYLD-transfected cells stimulated with TGF-β. FIG. 2d is a bar graph illustrating the relative quantity of PAI-1 mRNA expression compared with glyceraldehyde 3-phosphate dehydrogenase in siCon- or siCYLD-transfected cells stimulated with TGF-β. FIG. 2e is a pair of bar graphs showing SBE-promoter activity in A549 cells transfected with various amount of siCYLD or WT-CYLD and stimulated with TGF-β. FIG. 2f is a bar graph illustrating SBE-promoter activity in siCYLD or WT-CYLD-transfected human primary bronchial epithelial NHBE cells stimulated with TGF-β. FIG. 2g is a bar graph illustrating SBE-promoter activity in mouse MEFs from Cyld+/+ and Cyld−/− mice stimulated with TGF-β. FIG. 2h is a pair of bar graphs illustrating the relative quantity of mRNA expression of PAI-1 and CTGF compared with glyceraldehyde 3-phosphate dehydrogenase in the lung tissues of Cyld+/+ and Cyld−/− mice 6-h post-i.t. inoculation of TGF-β (25-100 ng per mouse). * $P<0.05$ values in (b-h) are the means±s.d. (n=3). Statistical data analysis was performed using Student's t-test. FIG. 2i is a series of photomicrographs of H&E and Masson's trichrome staining of lung tissues from Cyld−/− mice 2-weeks post-S. pneumoniae-infection with or without intraperitoneal inoculation of SB431542 (10 mg per kg body weight). Scale bars, 200 μm.

FIG. 3 illustrates CYLD inhibition of TGF-β-signalling via decreased stability of Smad3 protein. FIG. 3a is a bar graph illustrating SBE-promoter activity in siCon- or siCYLD-transfected TβII-deficient DR26 cells co-transfected with control vector or constitutively active (C/A)-TβRI. FIG. 3b is a bar graph illustrating SBE-promoter activity in siCON- or siCYLD-transfected TβI-deficient R1B cells co-transfected with control vector or WT-Smad3. FIG. 3c is a bar graph illustrating SBE-promoter activity in siCON- or siCYLD-transfected Smad3−/− MEF cells, co-transfected with control vector or WT-Smad3. FIG. 3d is a pair of immunoblots illustrating cells transfected with siCYLD or WT-CYLD treated with TGF-β and analysed by immunoblotting with the indicated antibodies. In the immunoblots of FIGS. 3e and 3f, MEF cells and lung tissues from Cyld+/+ and Cyld−/− mice were analysed by immunoblotting with the indicated antibodies. In the panel of photomicrographs of FIG. 3g, lung tissues from control (Con) and lung fibrosis patients (Fibrotic lung) were stained against Smad3 (Left panels, ×100; right panels, ×400). Scale bars, 200 μm. In the bar graph of FIG. 3h, cells transfected with WT-CYLD with (right panel) or without Flag-WT-Smad3 (left panel) were analysed by immunoblotting with the indicated antibodies. FIG. 3i is series of bar graphs illustrating the relative quantity of mRNA expression of PAI-1, CTGF, and Smad3 compared with glyceraldehyde 3-phosphate dehydrogenase in A549 cells transfected with siCON or siCYLD and stimulated with TGF-β. In the immunoblot of FIG. 3j, cells transfected with control vector or WT-CYLD were treated with MG132 (20 μM) and analysed by immunoblotting with the indicated antibodies. In the bar graph of FIG. 3k, cells transfected with WT-CYLD were pre-treated with MG-132, and relative quantity of PAI-1 mRNA expression, compared with glyceraldehyde 3-phosphate dehydrogenase, post-TGF-β-treatment. * P<0.05, # P>0.05 values in a, b, c, i, and k are the means±s.d. (n=3). Statistical data analysis was performed using Student's t-test.

FIG. 4 illustrates that CYLD decreases the stability of Smad3 protein in a GSK3β-CHIP-dependent manner possibly via Akt. FIG. 4a is an immunoblot illustrating cells transfected with WT-CYLD or DUB-deficient mutants (H/N-CYLD or C/S-CYLD) with the indicated antibodies. FIG. 4b is a bar graph showing SBE-promoter activity in cells transfected with WT-CYLD, H/N-CYLD or C/S-CYLD stimulated with TGF-β. FIG. 4c is an immunoblot illustrating cells co-transfected with siCon or siCHIP with WT-CYLD or H/N-CYLD with the indicated antibodies. FIG. 4d is a bar graph showing SBE-promoter activity in cells co-transfected with siCon or siCHIP with WT-CYLD stimulated with TGF-β. The bar graph of FIG. 4e shows the relative quantity of PAI-1 mRNA expression compared with glyceraldehyde 3-phosphate dehydrogenase in cells co-transfected with siCon or siCHIP with WT-CYLD stimulated with TGF-β. In FIG. 4f, cells transfected with control vector, WT-CYLD or DUB-deficient H/N-CYLD were treated with vehicle control or GSK3β-inhibitor SB216763 (5 μM) for 12 h and analysed by immunoblotting with the indicated antibodies. In FIG. 4g cells transfected with control vector or WT-CYLD were pre-treated with GSK3β-inhibitor (5 μM) for 2 h, followed by TGF-β-stimulation, and SBE-promoter activity was then determined. In FIG. 4h, recombinant GSK3β protein (His-GSK3β) was incubated either with GST or recombinant CHIP protein (GST-CHIP) in vitro. CHIP was pulled down with Sepharose 4B beads and immunoblotted against His to detect GSK3. In FIG. 4i, HA-GSK3β in cells co-transfected with Myc-CHIP and HA-GSK3β was pulled down with HA probe and analysed by immunoblotting with anti-Myc antibody. In FIG. 4j, A549 cells were treated with S. pneumoniae for various times as indicated in the figure, and cell lysates were analysed by immunoblotting with the indicated antibodies. In FIG. 4k, MEF cells from Cyld+/+ and Cyld−/− mice were treated with S. pneumoniae for 30 minutes, and cell lysates were analysed by immunoblotting with the indicated antibodies. In FIG. 4l, WT mice were i.t. inoculated with S. pneumoniae for various times as indicated in the figure, and proteins from lung tissues were analysed by immunoblotting with the indicated antibodies. In FIG. 4m, A549 cells were treated with S. pneumoniae for various times as indicated, and cell lysates were analysed by immunoblotting with the indicated antibodies. * P<0.05 values in b, d, e, and g are the means±s.d. (n=3). Statistical data analysis was performed using Student's t-test. S.p., Streptococcus pneumonia.

FIG. 5 illustrates that CYLD decreases Smad3 stability by inhibiting Akt. (a) MEF cells from Cyld+/+ and Cyld−/− mice were transfected with siCon or siAkt1/2 and analysed by immunoblotting with the indicated antibodies. (b) SBE-promoter activity was determined in siCYLD-transfected A549 cells with or without siAkt co-transfection and stimulated with TGF-β. (c) SBE-promoter activity was determined in MEFs from Cyld+/+ and Cyld−/− mice pretreated with Akt inhibitor and stimulated with TGF-β. (d) MEF cells from Cyld+/+ and Cyld−/− mice were incubated with Akt inhibitor (20 μM), and cell lysates were analysed by immunoblotting with the indicated antibodies. (e) Cells were incubated with Akt inhibitor (20 μM) or LY294002 (20 μM), and cell lysates were analysed by immunoblotting with the indicated antibodies. (f) Lysates from cells transfected with HA-CYLD and Flag-Akt were immunoprecipitated with anti-CYLD antibody (upper panel) or anti-Akt antibody (lower panel), and interacting proteins were analysed by immunoblotting. (g) A549 cells were treated with S. pneumoniae for various times as indicated in the figure, stained with rabbit anti-CYLD antibody, and/or mouse anti-Akt antibody, and in vivo protein-protein interaction between CYLD, and Akt was detected with secondary proximity probes, anti-Rabbit MINUS and antimouse-PLUS, using Duolink in vivo protein-protein interaction detection kit (Olink). Scale bar, 10 μm. (h) Cells were treated with S. pneumoniae or vehicle control. Akt in cell lysates was pulled down with anti-Akt antibody and immunoblotted against CYLD and Akt. * P<0.05 values in b, c are the means±s.d. (n=3). Statistical data analysis was performed using Student's t-test. S.p., Streptococcus pneumonia.

FIG. 6 illustrates CYLD deubiquitinates K63-polyubiquitinated Akt to reduce Smad3. (a) Lysates from A549 cells co-transfected with HA-Ub WT, Flag-Akt WT, Flag-WT-CYLD or Flag-H/N-CYLD were immunoprecipitated with anti-Akt antibody and analysed by immunoblotting with the indicated antibodies. (b) Cells were co-transfected with Flag-Akt, HA-CYLD, or siCYLD and treated with S. pneumoniae. Akt was pulled down with Flag probe and immunoblotted against Ubiquitin (Ub), Akt, and CYLD. (c) Cells transfected with control vector or Flag-WT-CYLD were treated with S. pneumoniae, and cell lysates were immunoprecipitated with anti-Akt1 antibody and analysed by immunoblotting with the indicated antibodies. (d) CYLD-depleted cellsusing siCYLD were treated with S. pneumoniae, and Akt in cell lysates was pulled down with anti-Akt antibody and immunoblotted against Ub, Akt, and CYLD. (e) Lysates from A549 cells co-transfected with Flag-Akt WT, Flag-WT-CYLD, HA-Ub WT, HA-Ub K63, or HA-Ub K48 were immunoprecipitated with anti-Akt antibody, and analysed by immunoblotting with the indicated antibodies. (f) Recombinant Akt1 (His-rAkt1) was incubated with recombinant K63 ubiquitin (His-rUb-K63) with or without recombinant CYLD (GST-rCYLD) in in vitro ubiquitination assay buffer (BostonBiochem) and analysed by immunoblotting with the indicated antibodies. (g) MEF cells from Cyld+/+ and Cyld−/− mice were co-transfected with Flag-Akt and HA-Ub K63, and treated with S. pneumoniae. Akt in cell lysate was pulled down with Flag probe and immunoblotted against Ub and Akt. (h) Lysates from cells co-transfected with HA-Ub K63, Flag-Akt WT, or Flag-Akt KR mutants (K8R, K14R, K20R or K30R) were immunoprecipitated with anti-Flag probe and analysed by immunoblotting with the indicated antibodies. (i) SBE-promoter activity was determined in A549 cells co-transfected with WT-CYLD, Akt WT, Akt K14R or Akt K20R stimulated with TGF-β. * P<0.05, # P>0.05 values in i are the means±s.d. (n=3). Statistical data analysis was performed using Student's t-test. S.p., Streptococcus pneumonia.

FIG. 7 is a schematic model illustrating a critical role of CYLD in lung fibrosis. On the one hand, following lung injury after severe bacterial infection (e.g., S. pneumoniae infection), extracellular matrix production and tissue recovery process are initiated via both TβRII/I-mediated activation of Smad3 and Akt-dependent inhibition of GSK3β-CHIP-mediated Smad3 degradation. On the other hand, CYLD induced by S. pneumoniae inhibits Akt by deubiquitinating K63-polyubiquitinated Akt, which in turn leads to activation of GSK3β and promotes CHIP-mediated Smad3 degradation, thereby attenuating excessive fibrotic response and preventing lung fibrosis (a). Deficiency of Cyld results in enhanced activation of Akt, which in turn leads to inhibition of GSK3β and CHIP-mediated Smad3 degradation, thereby promoting excessive fibrotic response and tissue fibrosis (b). ECM, extracellular matrix; TβRII/I, TGF-β receptor II and I.

DETAILED DESCRIPTION

Enormous effort has been expended over the past several decades toward developing anti-inflammatory agents, with most strategies focusing on direct targeting of the positive pathways (e.g., those including IκB kinase (IKK) to suppress inflammation. While these agents often showed reasonable efficacy, they have also exhibited significant adverse effects such as increasing the patient's susceptibility to infection and inducing apoptosis. These effects hamper further clinical development. As there has been limited success in developing therapies for long-term treatment of inflammatory disorders without significant side effects, there remains a need for methods of treating inflammation and other immune-related disease.

We have now found that up-regulating expression of CYLD, a key negative regulator of inflammation, by various strategies, including pharmacological inhibition of its own negative regulator, provides new ways to treat unwanted inflammation in a number of pathological conditions. Moreover, it is our expectation that the strategies described herein will not cause the serious adverse effects often seen when positive regulators of inflammation are targeted. Thus, an advantage of the present methods may be in maintaining the patient's defense responses.

Targeting CYLD:

Recent studies have identified CYLD (cylindromatosis) as a key inducible negative feedback regulator of bacteria-induced inflammation (Sun, Nature Rev. Immunol. 8:501-511, 2008 and Wang et al., Cell. Mol. Immunol. 9:131-135, 2012). CYLD is a deubiquitinase that has been shown to act as a negative regulator for various signaling pathways, including TRAF6, NEMO and Akt by removing lysine 63-linked polyubiquitin chains from several specific substrates (Lim et al., Nature Commun. 3:771, 2012; Sun, Cell Death Differ. 17:25-34, 2010). The expression of CYLD is relatively low under physiological conditions but is significantly up-regulated upon bacterial infections in respiratory systems (Jono et al., J. Biol. Chem. 279:36171-36174, 2004; Lim et al., PLoS One 2, e1032, 2007; and Yoshida et al., J. Biol. Chem. 280:4111-41121, 2005). In contrast, low expression of CYLD has also been reported in tumors (Massoumi, Future Oncol. 7:285-297, 2011, and Espinosa et al., Cancer Cell 18:268-281, 2010). The structure of the CYLD gene, including its sequence and intron-exon boundaries, and the structure and function of the encoded deubiquitinase are well understood. See, for example, Reiley et al. (J. Biol. Chem. 279:55161-55167, 2004).

CYLD has been extensively studied in respiratory bacterial infections, especially infections caused by nontypable Haemophilis influenza (NTHi), and we use this model system in some of the studies described below. NTHi and other co-agonists can synergistically induce robust inflammation in infected tissue, and CYLD negatively regulates many of the pathways induced during infection. For example, CYLD is a deubiquitinating enzyme that has been implicated in the downregulation of NFkB. It contains ubiquitin carboxy-terminal hydrolases that bind to ubiquitin and detach it from a target protein. Ubiquitin, a small regulatory protein that is present in all eukaryotic cells, attaches to other proteins, leading either to their activation or degradation.

Upregulating the expression or activity of CYLD in a subject or organism can be accomplished by administering to the subject an effective amount of a pharmaceutical composition that includes, as the sole active ingredient or as one of a plurality of active ingredients, an agent that upregulates the expression of the gene cylindromatosis (CYLD) or the activity of the encoded deubiquitinase. Such upregulation can be accomplished by administering a nucleic acid construct that expresses CYLD or that down-regulates the expression or activity of a negative regulator of CYLD (such as a phosphodiesterase 4 (PDE4 (e.g., PDE4B) or the c-jun N-terminal kinase 2 (JNK2)). The reduction of gene and/or protein expression or activity relieves or prevents, to a clinically beneficial extent, a medical condition as described herein or a sign or symptom thereof.

As noted above, any of a wide variety of expression vectors can be used to carry CYLD-encoding, PDE4B-inhibiting, JNK2-inhibiting, or Akt-modulating nucleic acid sequences. The vector can be, for example, a plasmid, cosmid, or viral vector. Expression can be regulated using standard control elements, such as a promoter, which may allow for constitutively active or inducible expression. The promoter can also be one that drives tissue-specific expression. In addition to the promoter, the expression vector can contain a transcription unit or expression cassette that contains any and all of the additional elements required for the expression of the nucleic acid in a host cell (e.g., in affected cells within the patient). A typical expression cassette contains a promoter that is operably linked to the nucleic acid sequence encoding the desired product, and to the signals required, for example, for efficient polyadenylation of the transcript, transcriptional termination, ribosome binding sites, or translation termination. Additional elements of the construct or cassette may include an enhancer and exogenous spliced intronic signals. Any of the well known procedures for introducing nucleotide sequences into host cells may be used in the context of this invention. These include the use of calcium phosphate transfection, polybrene, protoplast fusion, electroporation, liposomes, microinjection, naked DNA, plasmid vectors, viral vectors, both episomal and integrative, and any of the other well known methods for introducing cloned genomic DNA, cDNA, synthetic DNA or other foreign genetic material into a host cell (see, e.g., Sambrook et al., "Molecular Cloning: A Laboratory Manual," Second edition, Cold Spring Harbor Laboratory Press, 1989; and Ausubel et al., "Current Protocols in Molecular Biology", John Wiley & Sons, New York, 1987 and periodic updates). The tissue-specific promoter can be selected to drive expression in a tissue or cell type affected by one of the conditions described herein (e.g., the respiratory system, the nervous system, the cardiovascular system, the reproductive or genitourinary system, the gastrointestinal system, the skin, connective tissue, or the ears, nose, throat, or sinuses).

There is a similar wealth of knowledge regarding the production of protein biotherapeutics, including antibodies, that will specifically bind and inhibit PDE4B, JNK2, or Akt. An anti-PDE4B, anti-JNK2, or anti-Akt antibody used in the present compositions and methods can be a tetrameric antibody (e.g., an IgG (e.g., IgG1)), a single chain antibody, an Fab fragment, or an F(ab')2 fragment. The antibody can also be a human antibody, a humanized antibody, or a chimeric antibody. These and similar modified configurations are well known in the art.

Not only are the present anti-cancer, anti-inflammatory, and anti-fibrotic strategies applicable to a number of medical conditions, but it is also our expectation that they can be employed without the serious adverse effects often seen when positive regulators of inflammation are targeted.

Any of the compositions of the invention can be free from (i.e., they can exclude) an agent that modulates a positive regulator of inflammation. Similarly, any of the methods of the invention (particularly methods of treatment) can exclude a step in which the patient is treated with an agent that modulates a positive reglator of inflammation. For example, the present compositions can be free from steroids (e.g., glucocorticoids), from inhibitors of NFκB (e.g., pyrrolidine dithiocarbamate (PDTC)), and/or from inhibitors of the phosphatase PAC-1, and the present methods of treatment can lack a step in which steroids, inhibitors of NFκB, and/or PAC-1 are administered to a subject.

In infectious diseases such as OM, bacteria-induced inflammation is an essential bodily reaction for eradicating pathogens. However, if uncontrolled, excessive and/or prolonged inflammation is harmful to the host, owing to severe tissue damage caused thereby. Thus, inflammation must be tightly regulated.

In one embodiment, such upregulation is accomplished by introducing to a subject or patient in need thereof an agent that upregulates the expression of CYLD in the form of a nucleic acid construct that expresses CYLD, or a biologically active variant thereof (e.g., a biologically active fragment thereof or a substitution mutant).

Targeting PDE4 or JNK2:

In a further embodiment, the present invention provides methods for treating an inflammatory condition by upregulating CYLD through administering an inhibitor of phosphodiesterase 4 (PDE4) or an inhibitor of c-jun N-terminal kinase 2 (JNK2). In still a further aspect, the inhibitor of PDE4 is one that is specific for (or selective for) the isotype PDE4B, for example an inhibitor that will inhibit a PDE4B (e.g., PDE4B1, PDE4B2, PDE4B3, or PDE4B4) but will not inhibit another isoform (e.g., a PDE4D such as PDE4D1-PDE4D9) to any significant extent. One of ordinary skill in the art will understand the structural and functional differences between various phosphodiesterases and can consult any number of publications regarding this family (for example, Halpin, Int. J. of COPD 3(4):543-561, 2008).

The present inventors have determined that phosphodiesterase 4 (PDE4) plays a critical role in mediating inflammation via inhibiting CYLD, the key negative regulator for OM inflammation, and thus provide important insight into the tight regulation of inflammation and a target for therapeutic agents therefor. The PDE superfamily comprises 11 subfamilies, namely PDE1-PDE11 in mammals. They act as important positive and negative regulators of cellular response. To date, a number of PDE inhibitors have been successfully developed as drugs in the clinic, e.g. Viagra® (targeting PDE5) for erectile dysfunction and roflumilast (targeting PDE4) for asthma and COPD. However, the available nonspecific PDE4 inhibitors (targeting all four subfamily members A-D) have exhibited intolerable adverse effects, e.g. emesis, due to its inhibitory effect on PDE4D. Moreover, inhibition of PDE4D caused impaired growth. Thus, identifying PDE4B, but not PDE4D, as a key regulator and therapeutic target for inflammation provides a therapeutic target for more tolerable anti-inflammatory agents that selectively and specifically target PDE4B, and not PDE4D, for treating inflammatory diseases.

Examples of known, useful PDE4B inhibitors include rolipram, roflumilast, and cilomilast. Roflumilast, for example, is a potent and more specific inhibitor for PDE4B, and is currently clinically available for the treatment of asthma and COPD.

Other useful inhibitors are those described in WO 2007/142929 (the entire content of which is incorporated by reference herein). These inhibitors include a substituted benzene or substituted six-membered heteroaryl rings comprising one or two ring nitrogens, the substitution comprising an ether, thioether, or amine group in which the alkyl group on the ether, thioether, or amine is a haloalkyl group. The haloalkyl group can be a fluoromethyl, difluoromethyl, or trifluoromethyl group.

Further, studies have shown that two major MAP kinase JNK family members, JNK1 and JNK2, are ubiquitously expressed in various human tissues, including the middle ear, while JNK3 is selectively expressed in neurons. It has been traditionally thought that JNK1 and JNK2 are functionally redundant, but recent studies showed that they are selectively activated and play distinct functional roles. However, the mechanisms underlying the selective activation remain unknown. The present inventors have found that PDE4 (in particular, PDE4B) selectively activates JNK2, but not JNK1. Identifying the role of JNK2 but not JNK1 in mediating PDE4B-mediated inflammation by inhibiting CYLD provides a further therapeutic target for treatment with selective JNK2 inhibitors to suppress OM inflammation, and minimize the adverse side effects caused by concommitent inhibition of JNK1 such as cell growth.

As noted, the inhibitor of PDE4 can be one that inhibits PDE4B but does not significantly inhibit another PDE4-family member (e.g., PDE4D). To selectively inhibit PDE4B, one can administer a nucleic acid (e.g., a nucleic acid construct) that inhibits PDE4B gene expression. Such nucleic acids are known in the art and include antisense oligonucleotides, microRNAs, and nucleic acids that mediate RNAi (e.g., siRNAs and shRNAs).

The agent that upregulates the expression of CYLD in the compositions and methods of the invention can be an inhibitor of JNK2. For example, the inhibitor of JNK2 can be a JNK interacting protein (JIP) or a peptide fragment thereof, optionally linked to the cell-penetrating peptide TAT (as described, for example, in Kaoud et al. (*ACS Chem. Biol.* 6:658-666, 2011)) or a 2,4-diaminopyrimidine (as described, for example, in Song et al. (*Med. Chem. Commun* 3:238-243, 2012)). The inhibitor of JNK2 can also be a nucleic acid that inhibits JNK2 gene expression.

Where the present compositions include a small molecule (a chemical compound), the compositions can include the molecule or compound or a "pharmaceutically acceptable salt" thereof. We use this term to refer to salts of the compounds described herein that retain their biological effectiveness and which are not biologically or otherwise undesirable. Such pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri (cycloalkenyl) amines, substituted cycloalkenyl amines, disubstituted cycloalkenyl amine, trisubstituted cycloalkenyl amines, aryl amines, diaryl amines, and the like. The salt can also be an acid addition salt.

The invention features methods of treating a patient (or subject) who is suffering from a medical condition associated with inflammation. The method comprises administering to the patient a therapeutically effective amount of a pharmaceutical composition comprising an agent that downregulates the expression of the Akt gene or inhibits the activity of the encoded kinase. Such conditions include, but are not limited to: (1) inflammation of a reproductive organ (e.g., prostatitis, pelvic inflammatory disease, or an infectious disease that causes inflammation of a reproductive organ); (2) an autoimmune disease, particularly psoriasis or rheumatoid arthritis; or (3) upper and lower respiratory diseases or conditions, such as otitis media, rhinitis, sinusitis, or an infectious disease that causes inflammation of the ears, nose, nasal passage, or throat.

As described above, the methods encompass the treatment of a wide variety of subjects, including infants and children. The agent that downregulates the expression of the Akt gene can be a nucleic acid that inhibits the Akt gene (e.g., an antisense oligonucleotide, a microRNA, or a nucleic acid that mediates RNAi). In one embodiment, the agent that inhibits the activity of the encoded kinase can be a nucleic acid construct that expresses an enzyme that deubiquitinates Akt (e.g., the enzyme CYLD). In another embodiment, the agent that inhibits the activity of the encoded kinase can be VQD-002, perifosine, or miltefosine. As noted, the pharmaceutical composition can be formulated for ototopic administration in the case of an ear condition.

Otitis Media is a Condition Amenable to Treatment as Described Herein.

In one embodiment, the invention provides methods for treating a patient who is suffering from a medical condition associated with inflammation of the ears, nose, nasal passages, or throat, and comprises administering to the patient a therapeutically effective amount of a pharmaceutical composition comprising an agent that upregulates the expression of the gene cylindromatosis (CYLD) or the activity of the encoded deubiquitinase, CYLD. The methods can result in a reduction of inflammation or another symptom. For example, in treating otitis media, the present methods can also reduce mucosal thickening in the middle ear and polymorphonuclear neutrophil (PMN) infiltration in the middle ear mucosa.

Conditions amenable to treatment as described herein include upper respiratory infections that cause otitis media, rhinitis, sinusitis, or an infectious disease that leads to inflammation of the ears, nose, nasal passage (or a part thereof), throat or lung. The infectious disease can be associated with a bacterial or viral pathogen (e.g., a bacterium of the genus *Streptococcus* (e.g., *S. pneumoniae*, sometimes called *pneumococcus*, or *S. pyogenes*) or a virus (e.g., a respiratory syncytial virus or an influenza virus).

In a particular embodiment, such condition is otitis media (OM), an infection of the middle ear, commonly caused by infection with nontypeable *Haemophilus influenzae* (NTHi). Otitis media is the most common childhood bacterial infection and also the leading cause of conductive hearing loss in children. Annually, there are 24.5 million visits to physician's offices for OM in the U.S. Over $5 billion is spent annually for the care of OM. Approximately 10% of acute OM progresses to chronic OM, a leading cause of conductive hearing loss in children in the U.S. Since OM causes hearing loss during a crucial period for speech and language development, children who have had early hearing impairment due to frequent middle ear infections may later suffer speech and language disabilities. Despite an obvious need for prophylactic measures, development of highly effective vaccines for OM still remains a challenge. Moreover, inappropriate antibiotic treatment of OM has increased antibiotic resistance substantially. Due to its high prevalence, its long-term sequelae, and cost to society as a whole, the NIH/NIDCD has designated OM as an important area for research.

Currently, there are no effective therapeutic agents available for treating OM due to poor understanding of the molecular pathogenesis of OM. Inflammation is a hallmark of OM. However, there are no effective therapeutics, including anti-inflammatory agents, available for treating the adverse consequences of an excessive inflammatory response in OM, and until now, how inflammation is tightly regulated in OM was largely unknown.

The present invention now provides insights into the negative feedback regulation of the inflammatory response in OM, and provides for methods of upregulating expression of CYLD, the key negative regulator of inflammation, in order to modulate, or reduce, an excessive or prolonged inflammatory response in OM patients, thereby preventing or inhibiting further tissue damage caused by the inflammatory process.

Furthermore, the identification of PDE4B as a key regulator and specific therapeutic target for inflammation in OM provides a unique target for new and existing drugs in the treatment of OM, while avoiding the adverse effects of previous targets of anti-inflammatories. In addition, ototopical administration of the clinically available PDE4 inhibitor, roflumilast, among others, in the treatment of OM is also advantageous by minimizing the side-effects caused by systemic administration.

In any of the methods requiring a pharmaceutical composition for treatment of a condition affecting the ears, the composition can be formulated for ototopic administration.

The OM pathology is not limited to that induced by nontypeable *Haemophilus influenzae* (NTHi); indeed, our data show that PDE4 also plays a critical role in regulating OM-induced by *S. pneumoniae*, another major OM pathogen, and inflammation induced by LPS and TNF-α. Thus the present invention is also applicable to these pathological and clinical situations as well.

Respiratory-Related Conditions.

Lung injury represents a major cause of morbidity and mortality worldwide. Injurious stimuli such as infectious agents and caustic chemicals initiate a complex and dynamic series of host wound-healing responses. During early stages of severe *S. pneumoniae* infections, pneumolysin induces acute lung injury (ALI) and lethality. As a critical host response, type 1 plasminogen activator inhibitor (PAI-1) is upregulated by *S. pneumoniae*, which provides protection against ALI by preventing alveolar hemorrhage 1. Appropriate host response such as upregulated PAI-1 production is thus critical for repairing injured lung tissue and restoring its function. However, if uncontrolled, excessive PAI-1 will have an adverse effect on tissue remodelling processes via enhanced accumulation of extracellular matrix in tissues. Thus, PAI-1 expression must be tightly and dynamically regulated during the entire host wound healing process. We previously found that deubiquitinase CYLD has a critical role in preventing excessive production of PAI-1 by suppressing its p38 MAPK-dependent expression. However, during lethal *S. pneumoniae* infection, excessive release of pneumolysin caused severe lung injury, which overwhelms the protective effect of available PAI-1, thereby leading to lethality. Interestingly, CYLD deficiency in Cyld-deficient mice results in excessive production of PAI-1, thus providing efficient protection against lethality. Therefore, our previous study demonstrates that CYLD is a critical negative regulator for host survival during the early stage of infection as Cyld-deficient mice have a much higher survival rate compared with wild-type (WT) mice. Because uncontrolled and excessive wound-healing responses such as excessive PAI-1 production could result in lung fibrosis, we hypothesized that Cyld-deficient mice survived lethal *S. pneumoniae* infection may develop lung fibrosis, and CYLD may thus act as a key regulator for wound-healing processes during the late stages of bacterial infection. In the studies described below, we show that CYLD acts as a critical negative regulator for an injury-induced fibrotic response by inhibiting transforming growth factor-β (TGF-β)-signalling. We further show that CYLD inhibits TGF-β signalling by decreasing the stability of Smad3 protein in a glycogen synthase kinase3-β (GSK3β)-Hsc70-interacting protein (CHIP)-dependent manner. Interestingly, CYLD decreases Smad3 stability by directly deubiquitinating K63-polyubiquitinated Akt. These studies bring new insights into the novel role of CYLD in regulating fibrosis and support methods aimed at identifying new therapeutic targets for treating these diseases.

Lung injury, whether induced by infection or caustic chemicals, initiates a series of complex wound-healing responses. If uncontrolled, these responses may lead to lung fibrotic diseases and loss of function. Thus, resolution of lung injury must be tightly regulated. The key regulatory proteins required fir tightly controlling resolution of lung injury have yet to be identified. We have shown that loss of deubiquitinase CYLD led to development of lung fibrosis in mice after infection with *Streptococcus pneumoniae*. CYLD inhibited transforming growth factor-β-signalling and prevented lung fibrosis by decreasing the stability of Smad3 in an E3 ligase carboxy terminus of Hsc70-interacting protein-dependent manner. Moreover, CYLD decreases Smad3 stability by deubiquitinating K63-polyubiquitinated Akt. Together, our results unveil a role for CYLD in tightly regulating resolution of lung injury and preventing fibrosis by deubiquitinating Akt. These studies may help develop new therapeutic strategy for preventing lung fibrosis.

Lung injury represents a major cause of morbidity and mortality worldwide. Injurious stimuli such as infectious agents and caustic chemicals initiate a complex and dynamic series of host wound-healing responses. During early stage of severe *Streptococcus pneumoniae* infections, pneumolysin induces acute lung injury (ALI) and lethality. As a critical host response, type 1 plasminogen activator inhibitor (PAL-1) is upregulated by *S. pneumoniae*, which provides protection against ALI by preventing alveolar hemorrhage. Appropriate host response such as upregulated PAI-1 production is thus critical for repairing injured lung tissue and restoring its function. However, if uncontrolled, excessive PAI-1 will have an adverse effect on tissue remodelling process via enhanced accumulation of extra cellular matrix in tissues. Thus, PAI-1 expression must be tightly and dynamically regulated during the entire host woundhealing process. We previously found that the deubiquitinase CYLD has a critical role in preventing excessive production of PAI-1 by suppressing its p38 MAPK-dependent expression. However, during lethal *S. pneumoniae* infection, excessive release of pneumolysin caused severe lung injury, which overwhelms the protective effect of available PAI-1, thereby leading to lethality. Interestingly, CYLD deficiency in Cyld-deficient mouse results in excessive production of PAI-1, thus providing efficient protection against lethality. Therefore, our previous study demonstrates that CYLD is a critical negative regulator for host survival during early stage of infection as Cyld-deficient mice have a much higher survival rate compared with wild-type (WT) mice. Because uncontrolled and excessive wound-healing response such as excessive PAI-1 production could result in lung fibrosis, we hypothesized that Cyld-deficient mice survived in lethal *S. pneumoniae* infection may develop lung fibrosis, and CYLD may thus act as a key regulator for wound-healing process during late stage of bacterial infections. Here we show that CYLD acts as a critical negative regulator for injury-induced fibrotic response by inhibiting transforming growth factor-β (TGF-β)-signalling, We further show that CYLD inhibits TGF-β-signalling via decreasing stability of Smad3 protein in a glycogen synthase kinase3-β (GSK3β)-Hsc70-interacting protein (CHIP)-dependent manner. Interestingly, CYLD decreases Smad3 stability by directly deubiquitinating K63-polyubiquitinated Akt (also known as protein kinase B, or PKB). These studies bring to light the unique role of CYLD in regulating fibrosis and allow for the identification of new therapeutic agents for treating these diseases.

Other respiratory diseases, traits, and conditions that could be treated in accordance with the present invention include, but are not limited to COPD, asthma, eosinophilic cough, bronchitis, sarcoidosis, pulmonary fibrosis, rhinitis, sinusitis, and/or other disease states associated with excessive inflammation activity in a subject or organism.

Other Conditions Amenable to Treatment:

The invention contemplates and encompasses methods of treating a wide variety of conditions by administering a composition as described herein, including a selective inhibitor of PDE4B (e.g., a nucleic acid that, through sequence-specific interaction, specifically inhibits the expression of PDE4B). Treatable conditions include cancer, inflammation, and fibrosis. In particular embodiments, the condition treated with a composition as described herein can be associated with inflammation of, or mucus overproduction in, the ears (either or both), the nose, or the throat, and may also affect the nasal passages, another area or tissue within the respiratory system (e.g., the lungs or bronchial tree), or a sinus cavity or passage extending from such a cavity. For example, the condition can be an interstitial lung disease, human fibrotic lung disease (e.g., idiopathic pulmonary fibrosis (IPF), cystic fibrosis, respiratory distress syndrome (adult (ARDS) or infant), tumor stroma in lung disease, systemic sclerosis, Hermansky-Pudlak syndrome (HPS), coal worker's pneumoconiosis (CWP), chronic pulmonary hypertension, AIDS-associated pulmonary hypertension, and the like, asthma, chronic bronchitis, chronic obstructive pulmonary disease (COPD), cough (e.g., eosinophilic cough), pulmonary fibrosis, rhinitis (e.g., allergic rhinitis), sinusitis, or otitis media. In other embodiments, the condition treated with a composition as described herein can be a human kidney disease. For example, a patient may have nephrotic syndrome, Alport's syndrome, HIV-associated nephropathy, polycystic kidney disease, Fabry's disease, a diabetic or other nephropathy, glomerular nephritis (e.g., chronic glomerulonephritis) or nephritis associated with systemic lupus. As noted, the present compositions can be effective against fibrosis, including fibrotic conditions in the liver (liver fibrosis), heart (myocardial fibrosis), and reproductive system (endometrial fibrosis). Where the liver is concerned, treatable conditions also include hepatitis (whether caused by a viral agent, autoimmune disease, or substance abuse), hepatic steatosis, and hepatic cirrhosis. In other embodiments, the condition treated with a composition as described herein can be a cardiovascular disease, including arterial restenosis and atherosclerosis, or a reperfusion injury of the myocardium. In other embodiments, the condition treated with a composition as described herein can be a cancer, and the present compositions can be used to impede tumor growth and/or metastasis. Particular cancers amenable to treatment include scleroderma, glioblastoma in Li-Fraumeni syndrome, sporadic glioblastoma, myeloid leukemia, acute myelogenous leukemia, myelodysplastic syndrome, myeloproliferative syndrome, cancers such as breast cancer, lung cancer, colon cancer (e.g., Lynch syndrome), prostate cancer or a gynecological cancer (e.g., ovarian or uterine cancer), and skin cancer (e.g., a melanoma or Kaposi's sarcoma). In addition to skin cancers or malignant proliferative skin diseases, the compositions of the invention can be used to treat eosinophilic granulomas, other benign skin diseases such as atopic dermatitis (a type of eczema) and urticaria (commonly known as hives), and scarring. In another embodiment, the present compositions and methods can be applied to a patient exhibiting metaplasia, which is generally understood to be a benign change that occurs in response to changes in milieu or chronic irritation. For example, cells and tissue within a patient's airway can exhibit metaplasia in response to smoke (e.g., smoke that is inhaled from a tobacco product such as a cigar or cigarette). While the invention is not so limited, in this instance, the irritant can cause the mucus-secreting ciliated pseudostratified columnar respiratory epithelial cells that line the airways to be replaced by stratified squamous epithelium. As noted, the present compositions can be effective against inflammatory conditions, including those that affect the gastrointestinal tract. These include inflammatory bowel disease (e.g., ulcerative colitis or Crohn's disease), and the present compositions are also useful in treating hypersecretion of gastric acid. In other embodiments, the condition treated with a composition as described herein can be a neurological disorder or an injury to the nervous system (e.g., the peripheral or central nervous system). For example, the condition can be a reperfusion injury of the brain, depression, memory impairment, monopolar depression, Parkinson's disease, Alzheimer's disease, Huntingtin's disease, spinal cord trauma, head injury, neurogenic inflammation, or pain. There is increasing evidence that neurodegenerative disorders and injuries have important inflammatory components, and any such disorders or injuries can be treated with the compositions described herein. In other embodiments, the condition treated with a composition as described herein can be an autoimmune disorder such as multiple sclerosis, rheumatoid arthritis, Grave's ophthalmopathy, psoriasis, or diabetes insipidus. Transplant rejection and graft versus host disease can also be treated. In other embodiments, the condition treated with a composition as described herein can be an infectious disease associated with a bacterial or viral pathogen. For example, the condition can be an infectious disease caused by a bacterium of the genus *Streptococcus* (e.g., *S. pneumoniae*, sometimes called *pneumococcus* or *S. pyogenes*), by nontypable *Haemophilus influenzae* (NTHi), or by *Pseudomas aeruginosa*. Other treatable infectious diseases are associated with a virus (e.g., a respiratory syncytial virus or an influenza virus). Hansen's disease, bacterial, fungal or viral induced sepsis or septic shock (endotoxic shock) can also be treated. In other embodiments, the condition treated with a composition as described herein can affect a reproductive or genitourinary tissue or organ. For example, the patient can be one who is suffering from a medical condition associated with inflammation of a reproductive organ (e.g., prostatitis, pelvic inflammatory disease, or an infectious disease that causes inflammation of a reproductive tissue or organ). In other embodiments, the condition treated with a composition as described herein can affect the skeletomuscular system. For example, a patient may be suffering from inflammatory arthritis, osteoarthritis, osteoporosis, inflammation and cytokine-mediated chronic tissue degeneration, muscle wasting, cachexia, or ankylosing spondylitis. In other embodiments, the condition treated with a composition as described herein can be drug induced ergotism, allergic conjunctivitis, vernal conjunctivitis, obesity, or pancreatitis.

In one embodiment, the invention features methods of treating a patient who is suffering from a medical condition associated with inflammation of a reproductive organ (e.g., prostatitis, pelvic inflammatory disease, or an infectious disease that causes inflammation of a reproductive organ). The methods can be carried out by administering to the patient a therapeutically effective amount of a pharmaceutical composition comprising an agent that upregulates the expression of the gene cylindromatosis (CYLD) or the activity of the encoded deubiquitinase. The agents can be those described above. Alternatively, or in addition, this patient population can also be treated with a therapeutically effective amount of a pharmaceutical composition comprising an agent that downregulates the expression of the Akt gene or inhibits the activity of the encoded kinase.

In another aspect, the invention features methods of treating a patient who is suffering from an autoimmune disease, particularly psoriasis or rheumatoid arthritis. The methods comprise administering to the patient a therapeutically effective amount of a pharmaceutical composition comprising an agent that upregulates the expression of the gene cylindromatosis (CYLD) or the activity of the encoded deubiquitinase. In these methods, any of the agents described above or elsewhere herein can be formulated for administration. As psoriasis affects the skin, the formulations intended for treatment of that condition can be topical.

Further, and as noted, these methods can be carried out using an inhibitor of PDE4 that inhibits PDE4B but does not significantly inhibit another PDE4-family member (e.g., PDE4D). These selective inhibitors can be nucleic acids (e.g., a nucleic acid construct) designed using methods known in the art to generate sequence-specific targeting molecules (e.g., antisense oligonucleotides, microRNAs, and nucleic acids that mediate RNAi (e.g., siRNAs and shRNAs)). In another embodiment, the agent that upregulates the expression of CYLD can be an inhibitor of JNK2.

In another embodiment, the invention features methods of treating a patient who is suffering from an autoimmune disease, particularly psoriasis or rheumatoid arthritis by administering to the patient a therapeutically effective amount of a pharmaceutical composition comprising an agent that downregulates the expression of the Akt gene or inhibits the activity of the encoded kinase.

In another embodiment, the invention features methods of treating a patient for obesity. The methods can include a step of administering to the patient a therapeutically effective amount of a pharmaceutical composition comprising an agent that upregulates the expression of the gene cylindromatosis (CYLD) or the activity of the encoded deubiquitinase. Agents useful in the treatment of obesity include any of those described herein. For example, these methods can be carried out using an inhibitor of PDE4 that inhibits PDE4B but does not significantly inhibit another PDE4-family member (e.g., PDE4D). For example, one can design an antisense oligonucleotide, microRNA, or nucleic acid that mediates RNAi (e.g., an siRNA or shRNA). In another embodiment, the agent that upregulates the expression of CYLD can be an inhibitor of JNK2. In another embodiment, one can administer a therapeutically effective amount of a pharmaceutical composition comprising an agent that downregulates the expression of the Akt gene or inhibits the activity of the encoded kinase.

The compounds of the invention can be useful in the prevention or treatment of a variety of human or other animal, including mammalian and non-mammalian disorders, including primarily inflammatory disorders and other immune-related diseases. It is contemplated that active molecules of the invention, such as a nucleic acid that selectively inhibits PDE4B expression, can be incorporated into any suitable carrier prior to use. The dose of active molecule, mode of administration and use of suitable carrier will depend upon the intended recipient and target disorder. The formulations, both for veterinary and for human medical use, of inhibitors according to the present invention typically include such inhibitors in association with a pharmaceutically acceptable carrier.

The active ingredients according to the invention are compounds that act to upregulate CYLD and may be one or more of: (1) PDE4 inhibitors (esp., PDE4B inhibitors); (2) inhibitors of JNK2; (3) Akt inhibitors; and may be nucleic acids (such as antisense oligonucleotides, microRNAs and a nucleic acid that mediates RNAi) or organic small molecule compounds. The active agents of the invention may be combined with other therapeutic compounds in a single formulation if desired.

Formulations and Dosages:

A therapeutically effective amount of a pharmaceutical composition of the present invention will depend upon a number of factors. For example, the species, age, and weight of the patient, the precise condition requiring treatment and its severity, and the nature of the formulation are all factors to be considered and understood as such by one of ordinary skill in the art. The amount administered will also likely depend on additional variables such as the relative biological efficacy of the active pharmaceutical agent delivered, the presence and types of excipients in the formulation, and the route of administration. Also, it is to be understood that the initial dosage administered can be increased beyond the above upper level in order to rapidly achieve the desired blood-level or tissue level, or the initial dosage can be smaller than the optimum and the daily dosage can be progressively increased during the course of treatment depending on the particular situation. If desired, the daily dose can also be divided into multiple doses for administration, for example, two to four times per day. The therapeutically effective amount ultimately prescribed can be varied at the discretion of the attending physician or veterinarian. For therapeutic agents useful in the present invention, at least some of which are already known in the art, the amount administered in the context of the conditions described herein can be guided by amounts previously used successfully. In therapeutic use for treating cancer, inflammation, fibrosis, or any of the particular conditions described herein, the pharmaceutical compositions will be administered orally, parenterally and/or topically at a dosage sufficient to obtain and maintain a concentration (i.e., an amount, blood-level or tissue level) of an active agent in the animal undergoing treatment which will be effective. Generally, an effective amount of dosage of the active agent will be in the range of from about 0.1 to about 100, more preferably from about 1.0 to about 50 mg/kg of body weight/day.

As described further below, the therapeutic agents described herein can be combined with one or more pharmaceutically acceptable carriers, diluents, or excipients, which are "acceptable" in the sense of being compatible with the other ingredients of the formulation and not deleterious to the patient being treated.

The formulations can conveniently be presented in dosage unit form (sometimes also referred to as "unit dosage form") and can be prepared by any of the methods well known in the art of pharmacy. In general, some formulations are prepared by bringing the pharmaceutical agents into association with a liquid carrier or a finely divided solid carrier or both, and then, if necessary, shaping the product into the desired formulation. The compositions for administration can be prepared by any of the methods well known in the pharmaceutical art, described, for example, in Remington's Pharmaceutical Sciences, (Gennaro, A., ed.), Mack Pub. (1990). Unit dosage forms can include, as a non-limiting example, 0.5 mg to 1g of a therapeutic agent as described herein, depending on the condition being treated, the route of administration, and the age, weight, and condition of the patient. Typical unit dosage formulations are those containing a daily dose or sub-dose, or an appropriate fraction thereof, of an active ingredient.

A pharmaceutical composition of the invention should be formulated to be compatible with its intended route of administration. Examples of routes of administration include oral or parenteral, for example, intravenous, intradermal, inhalation, transdermal (topical), transmucosal, ototopic, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide.

Pharmaceutical formulations may be adapted for administration by any appropriate route, for example by an oral (including buccal or sublingual), rectal, nasal, topical (including buccal, sublingual or transdermal), vaginal, or parenteral (including subcutaneous, intramuscular, intravenous or intradermal) route. Such formulations may be prepared by any method known in the art of pharmacy, for example by bringing into association the active ingredient with the carrier(s) or excipient(s). By way of example, and not meant to limit the invention, with regard to certain conditions and disorders for which the compounds of the present invention are believed useful, certain routes will be preferable to others.

Pharmaceutical formulations adapted for oral administration may be presented as discrete units such as capsules or tablets; powders or granules; solutions or suspensions, each with aqueous or non-aqueous liquids; edible foams or whips; or oil-in-water liquid emulsions or water-in-oil liquid emulsions. For instance, for oral administration in the form of a tablet or capsule, the active drug component can be combined with an oral, non-toxic pharmaceutically acceptable inert carrier such as ethanol, glycerol, water, and the like. Generally, powders are prepared by comminuting the compound to a suitable fine size and mixing with an appropriate pharmaceutical carrier such as an edible carbohydrate, as, for example, starch or mannitol. Flavorings, preservatives, dispersing agents, and coloring agents can also be present.

Capsules are made by preparing a powder, liquid, or suspension mixture and encapsulating with gelatin or some other appropriate shell material. Glidants and lubricants such as colloidal silica, talc, magnesium stearate, calcium stearate, or solid polyethylene glycol can be added to the mixture before the encapsulation. A disintegrating or solubilizing agent such as agar-agar, calcium carbonate or sodium carbonate can also be added to improve the availability of the medicament when the capsule is ingested. Moreover, when desired or necessary, suitable binders, lubricants, disintegrating agents, and coloring agents can also be incorporated into the mixture. Examples of suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like.

Lubricants useful in these dosage forms include, for example, sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

Tablets are formulated, for example, by preparing a powder mixture, granulating or slugging, adding a lubricant and disintegrant, and pressing into tablets. A powder mixture may be prepared by mixing the compound, suitably comminuted, with a diluent or base as described above. Optional ingredients include binders such as carboxymethylcellulose, aliginates, gelatins, or polyvinyl pyrrolidone, solution retardants such as paraffin, resorption accelerators such as a quaternary salt, and/or absorption agents such as bentonite, kaolin, or dicalcium phosphate. The powder mixture can be wet-granulated with a binder such as syrup, starch paste, acadia mucilage or solutions of cellulosic or polymeric materials, and forcing through a screen. As an alternative to granulating, the powder mixture can be run through the tablet machine and the result is imperfectly formed slugs broken into granules. The granules can be lubricated to prevent sticking to the tablet-forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Where appropriate, dosage unit formulations for oral administration can be microencapsulated. The formulation can also be prepared to prolong or sustain the release as for example by coating or embedding particulate material in polymers, wax or the like.

Oral fluids such as solutions, syrups, and elixirs can be prepared in dosage unit form so that a given quantity contains a predetermined amount of the compound. Syrups can be prepared, for example, by dissolving the compound in a suitably flavored aqueous solution, while elixirs are prepared through the use of a non-toxic alcoholic vehicle. Suspensions can be formulated generally by dispersing the compound in a nontoxic vehicle. Solubilizers and emulsifiers such as ethoxylated isostearyl alcohols and polyoxy ethylene sorbitol ethers, preservatives; flavor additives such as peppermint oil, or natural sweeteners, saccharin, or other artificial sweeteners; and the like can also be added.

Suitable packaging for the pharmaceutical solution formulations may be all approved containers intended for parenteral use, such as plastic and glass containers, ready-to-use syringes and the like. In an embodiment, the container is a sealed glass container, such as a vial or an ampoule. A hermetically sealed glass vial is one example of a sealed glass container. According to an embodiment of the present invention, there is provided, in a sealed glass container, a sterile, injectable solution comprising a compound of the present invention in a physiologically acceptable solvent, and which has an appropriate pH for stability. Acid salts of the compounds of the present invention may be more soluble in aqueous solutions than their free base counter parts, but when the acid salts are added to aqueous solutions the pH of the solution may be too low to be suitable for administration. Thus, solution formulations having a pH above pH 4.5 may be combined prior to administration with a diluent solution of pH greater than 7 such that the pH of the combination formulation administered is pH 4.5 or higher. In one embodiment, the diluent solution comprises a pharmaceutically acceptable base such as sodium hydroxide and the pH of the combined formulation administered is between pH 5.0 and 7.0. One or more additional components such as co-solubilizing agents, tonicity adjustment agents, stabilizing agents and preservatives, for instance of the kind previously specified, may be added to the solution prior to passing the solution through the sterilizing filter.

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations may be applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouthwashes.

Pharmaceutical formulations adapted for nasal administration, where the carrier is a solid, include a coarse powder having a particle size for example in the range 20 to 500 microns. The powder is administered in the manner in which snuff is taken, i.e., by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered dose pressurized aerosols, nebulizers, or insufflators.

Further, the compositions of the present invention may also be in the form of suppositories for rectal administration of the compounds of the invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example. Pharmaceutical formulations adapted for rectal administration may be presented as suppositories or as enemas.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and solutes that render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use.

Extemporaneous injection solutions and suspensions may be prepared from sterile powders, granules, and tablets.

In addition to the ingredients particularly mentioned above, the formulations may include other agents conventional in the art having regard to the type of formulation in question. For example, formulations suitable for oral administration may include flavoring or coloring agents.

Identification of New Therapeutic Agents.

In another aspect, the invention provides methods of identifying putative pharmaceutical agents (e.g., anti-cancer, anti-inflammatory agents, or anti-fibrotic agents). The methods comprise the steps of: (a) providing a test agent; (b) exposing the agent to PDE4B and, concurrently or separately, to another PDE (e.g., PDE4D); and (c) assaying the level of expression of the genes encoding PDE4B and the other PDE (e.g., PDE4D) and/or the level of expression or activity of the encoded phosphodiesterases. An agent that inhibits the expression or activity of PDE4B but does not significantly inhibit the expression or activity of the other PDE assayed (e.g., PDE4D) is a putative anti-cancer, anti-inflammatory, or anti-fibrotic agent for the treatment of cancer, inflammation, or fibrosis, or of any of the medical conditions that are described herein or are found to otherwise benefit from the anti-inflammatory action of PDE4B inhibition. In another assay, one can carry out the steps comprising: (a) providing a test agent; (b) exposing the agent to a cell expressing Akt; and (c) assaying the level of expression of the gene encoding Akt, the encoded protein's degree of ubiquitination, or its activity. An agent that modulates (e.g., inhibits) the expression, degree of ubiquitination, or activity of Akt is a putative anti-cancer, anti-inflammatory, or anti-fibrotic agent.

EXAMPLES

Example 1. Inhibition of PDE4 Up-Regulates CYLD Expression

Phosphodiesterases (PDEs) have been recognized as therapeutic targets. Indeed, a number of PDE inhibitors have been successfully developed as effective therapeutic agents (e.g. VIAGRA® for treating erectile dysfunction by targeting PDE5 and roflumilast for asthma and COPD by targeting PDE4). For this reason, we initially sought to determine if PDEs act as key negative regulator for CYLD. Because PDE1 and PDE4 are selectively expressed in the middle ear (ME), we first evaluated the effects of specific PDE1 and 4 inhibitors on up-regulation of CYLD induced by the major OM bacterial pathogen NTHi. Interestingly, pharmacologic inhibition of PDE4 using the general PDE4 inhibitors rolipram and Ro20-1724 markedly enhanced NTHi-induced up-regulation of CYLD at both mRNA and protein levels in human middle ear epithelial cell HMEEC, lung epithelial cell A549 and human primary bronchial epithelial NHBE cultured under both conventional and air-liquid-interface culture conditions. Similar results were also found from the cells treated with four additional commonly used clinical NTHi strains (1479, 2019, 3198 and 9274). Similarly, rolipram also enhanced up-regulation of CYLD at the mRNA level and protein level in the middle ear mucosa of a well-established mouse model of OM as assessed by performing real-time Quantitative PCR (Q-PCR) and immunofluorescence (IF) staining using a CYLD-specific antibody. In contrast, a PDE1 specific inhibitor exhibited no effect on CYLD up-regulation. These data suggest that PDE4 acts as a key negative regulator for CYLD.

Example 2. Inhibition of PDE4 Leads to Suppression of NTHi-Induced Inflammation

We next determined if PDE4 inhibition suppresses NTHi-induced inflammation. As expected, the PDE4 inhibitor rolipram potently inhibited NTHi-induced NF-κB activation and up-regulation of pro-inflammatory mediators including IL-1β, IL-8 and TNF-α at the mRNA and the protein levels in cells assessed by Q-PCR and ELISA (specifically, in middle ear epithelial HMEEC, lung epithelial A549, and primary NHBE cells). Consistently, rolipram also inhibited NTHi-induced up-regulation of the proinflammatory mediators in the middle ear of mouse.

Intraperitoneal (i.p.) administration of rolipram also inhibited NTHi-induced typical otoscopic pathological changes of OM, including congestion and swelling of tympanic membranes and mucous effusion accumulation inside bulla as assessed by performing otoscopic examination in NTHi-inoculated mice. Moreover, it also inhibited middle ear mucosal thickening and polymorphonuclear neutrophil (PMN) infiltration in the middle ear mucosa, the key characteristic pathological changes of OM as assessed by performing histopathologic analysis.

Despite showing that inhibiting PDE4 enhanced up-regulation of CYLD and suppressed NTHi-induced inflammation, it was still unclear whether inhibiting PDE4 suppressed inflammation by up-regulating CYLD or by inhibiting a positive regulator of inflammation (e.g., IKKβ). We found that the PDE4 inhibitor rolipram no longer inhibited NTHi-induced up-regulation of the pro-inflammatory markers IL-1β, IL-8 and TNF-α in HMEEC, A549 and primary NHBE cells in which CYLD was depleted with siRNA CYLD. Similarly, rolipram also failed to inhibit NTHi-induced mRNA expression of these cytokines in CYLD-deficient cells. Moreover, similar results were also confirmed in a mouse OM model. Further, rolipram (by i.p. administration) no longer inhibited NTHi-induced up-regulation of IL-1β and MIP-2 (a mouse homologue of human IL-8) and middle ear mucosal thickening and PMN infiltration in the middle ear mucosa. These data suggest that inhibiting PDE4 suppresses inflammation by up-regulating CYLD.

We next determined if PDE4 inhibitors may also suppress inflammation via directly inhibiting IKKβ, the key positive regulator of NF-κB-dependent inflammation. Rolipram did not significantly inhibit activation of NF-κB induced by overexpressing either a constitutively active form of IKKβ or wild-type p65, the key sub-unit of NF-κB.

Example 3. PDE4B is Involved in Negatively Regulating NTHi-Induced Inflammation

We next sought to determine which PDE4 subfamily member is specifically involved. PDE4 consists of 4 subfamily genes, PDE4A to D, encoding rolipram-sensitive PDEs. PDE4 exerts its cellular functions by catalyzing and degrading cAMP, one of the most important second messengers in regulating numerous pathological processes in response to stimulants (e.g., bacterial pathogens). We determined that PDE4B is selectively and markedly up-regulated by NTHi at mRNA and protein levels in HMEEC cells in vitro and in the middle ear mucosa of mice in vivo as well as in primary airway epithelial NHBEs and the cell line A549. Consistent with these results, PDE4B enzymatic activity is also up-regulated by NTHi.

Together, these data suggest that PDE4B plays an important role in regulating NTHi-induced inflammation. Interestingly, a clinically available drug, roflumilast, known as a potent PDE4 inhibitor more selective for PDE4B than for PDE4D, also markedly suppressed NTHi-induced inflammatory response in HMEEC cell at a concentration much lower (10-times lower, 1 μM) than rolipram (10 μM). In contrast, cilomilast, a more PDE4D selective inhibitor than PDE4B exhibited no significant inhibitory effect on NTHi-induced inflammation. These findings are of particular translational and clinical significance as the current clinically available general PDE4 inhibitors have serious adverse effects mainly due to their inhibitory effects on PDE4D.

Example 4. Involvement of the JNK2 Pathway

We next sought to determine how PDE4B mediates NTHi-induced inflammation via inhibiting CYLD. Because MAP kinases (MAPKs) play an important role in mediating NTHi-induced host responses, we determined the involvement of MAPKs in regulating CYLD using specific inhibitors for various major MAPKs.

Inhibitors for MAPK JNK (SP600125) (1 μM) but not for ERK or p38 enhanced up-regulation of CYLD by NTHi and suppressed inflammation as expected in HMEEC cells in vitro and middle ear of mouse in vivo. Interestingly, PDE4 inhibitor no longer further enhanced NTHi-induced up-regulation of CYLD and suppressed inflammation in HMEEC that were already pretreated with JNK inhibitor. Because JNK1 and 2 represent the two major isoforms expressed in middle ear epithelial cells, we next determined which isoform is involved. The PDE4 inhibitor selectively inhibited NTHi-induced activation of JNK2; neither JNK1 nor other MAPKs were inhibited. These interesting findings thus led us to further determine if PDE4B suppresses CYLD expression and mediates NTHi-induced inflammation via selective activation of the JNK2, but not the JNK1 pathway. Moreover, JNK inhibitor also no longer inhibited NTHi-induced inflammation in CYLD-deficient cells. These data suggest that PDE4 negatively regulates CYLD and mediates inflammation via the JNK2 pathway.

Example 5. Ototopical Post-Inoculation Administration of a General PDE4 Inhibitor The data above demonstrate that the general PDE4 inhibitor, rolipram, when pre-administered systemically, up-regulates CYLD and suppresses subsequent inflammation in a mouse OM model. These data thus prompted us to directly test if post-inoculation administration of rolipram has any therapeutic effect on treating middle ear inflammation under clinically relevant condition. Ototopical administration works effectively when the eardrum is perforated either pathologically or surgically by tympanostomy tube insertion. Thus, we first determined if ototopical administration of rolipram up-regulates CYLD and suppresses inflammation in the middle ear of mice post NTHi inoculation. Interestingly, both ototopical pre- and post-inoculation administration of rolipram up-regulated CYLD and suppressed inflammation in a mouse OM model in vivo.

Example 6. PDE4B Inhibition In Vitro Using siRNA and KO Cell Approaches

Since we already showed that roflumilast, a potent and more PDE4B specific inhibitor, enhanced CYLD expression and inhibited NTHi-induced inflammation, we can directly determine if PDE4B acts as a critical regulator for suppressing CYLD expression and mediating NTHi-induced inflammation in vitro by inhibiting PDE4B using PDE4B specific siRNA and also PDE4B knockout (KO) cell approaches.

Q-PCR and Western blot can be used to monitor knockdown efficiency or deficiency. PDE4B assay can be performed to monitor the inhibition of PDE4B activity. Their effects on CYLD expression can be assessed using Q-PCR and Western Blot and the effects on inflammatory responses can be assessed using a luciferase reporter assay, Q-PCR, and ELISA as described. In addition to HMEEC cells, we can confirm the key findings using human primary NHBE cultured under routine and air-liquid interface. Moreover, other common NTHi clinical strains 1479, 2019, 3198 and 9274 can be used to confirm the generalizability of our findings obtained using strain 12.

Example 7. CYLD is a Key Negative Regulator for Lung Fibrosis

We began this study by first determining whether CYLD deficiency leads to development of lung fibrosis in a mouse model of lung injury induced by S. pneumoniae infection. As shown in FIG. 1a, a majority of WT mice that survive ALI appeared fully recovered without significant pathological changes. In contrast, Cyld−/− mice exhibited marked fibrotic pathological changes as evaluated by performing H & E staining. Further, histological analysis with Trichrome staining demonstrated significant collagen deposition (stained blue) in lungs of *S. pneumoniae*-inoculated Cyld−/− mice but not in WT mice. Moreover, *S. pneumoniae*-inoculated lungs of Cyld−/− mice also exhibited a hyperfibrotic response, with increased expression of fibrogenic gene type I and type III collagens (COL1A2 and COL3A1), connective tissue growth factor (CTGF) and PAI-1 compared with WT mouse lung (FIG. 1b). Similarly to the lethal dose of *S. pneumoniae*, a sub-lethal dose of *S. pneumoniae* still exhibited fibrotic effect, and the fibrotic response was significantly enhanced in Cyld−/− mice compared with WT mice. Thus, it is evident that, regardless of the severity of infection, CYLD has a critical role in tightly controlling the fibrotic response and preventing fibrosis. On the basis that CYLD acts as a negative regulator for PAI-1 upregulation by inhibiting p38 MAPK-dependent PAI-1 expression 1, we first determined whether CYLD inhibits *S. pneumoniae*-induced lung fibrosis also via inhibiting p38 MAPK signalling. Interestingly, treatment with p38-specific inhibitor SB203580 did not affect lung fibrosis in these Cyld−/− mice. This unexpected finding thus led us to focus on determining a p38-independent molecular mechanism by which CYLD prevents development of lung fibrosis post-bacterial-infection.

Among a number of signalling pathways involved in lung fibrosis, TGF-β-Smad signalling is crucial for regulating lung fibrosis, and *S. pneumoniae* has been shown to induce TGF-β-signalling. Thus, we first determined whether *S. pneumoniae* induces TGF-β-expression. *S. pneumoniae* induced TGF-β expression at late stage of infection when fibrosis develops, whereas it induced rapid p38 MAPK activation at an early stage when lung injury is induced, followed by inactivation at late stage. These interesting results may well explain why inhibition of p38 using a specific inhibitor did not affect lung fibrosis in Cyld−/− mice and may also imply an important role of TGF-β-Smad in mediating *S. pneumoniae*-induced lung fibrosis.

To further determine the clinical relevance of our findings in a mouse model, the expression level of CYLD protein in the lung of human patients with lung fibrosis was measured and compared with that in normal controls. As shown in FIG. 1 c, CYLD expression in the lung tissues with fibrosis was much lower compared with that in normal control. We next sought to explore why CYLD protein levels are lower in patients with fibrosis. Because TGF-β-expression was found to be upregulated at a later stage of infection during the recovery process from tissue injury, we sought to determine whether TGF-β regulates CYLD expression. Indeed, the expression of CYLD was inhibited by TGF-β in the lung tissues of mice. Thus, it is logical to propose that TGF-β may promote tissue fibrosis not only by activating the TGF-β-Smad signalling pathway, the critical positive regulator for fibrotic response, but may also, at least in part, by inhibiting the expression of CYLD, the negative regulator for fibrotic response.

To further evaluate the generalizability of our findings, we next sought to determine whether CYLD also acts as a key negative regulator for chemical-induced lung fibrosis in a widely used lung fibrosis model induced by bleomycin. Interestingly, bleomycin-induced lung fibrosis was also significantly enhanced in Cyld-deficient mice compared with WT mice. These data thus suggest that the anti-fibrotic effect of CYLD via inhibiting TGF-β-signalling may be generalizable for tissue fibrosis induced by other injurious stimuli as well.

Example 8. CYLD Prevents Lung Fibrosis Via Inhibiting TGF-β-Signalling

Because *S. pneumoniae* induces TGF-β-signalling and TGF-β-signalling is known as a crucial signalling pathway involved in the development of lung fibrosis, we determined whether CYLD inhibits TGF-β-signalling using various approaches including short interfering RNA (siRNA). As expected, siRNA-CYLD (siCYLD) efficiently reduced endogenous CYLD protein expression in a number of cell types including human primary bronchial epithelial NHBE cells and greatly enhanced TNF-α-induced activation of NF-κB-Luc activity, as previously shown (FIG. 2a, 2b). Interestingly, CYLD knockdown with siCYLD markedly enhanced the activity of TGF-β-induced Smad-binding element (SBE)-dependent promoter and TGF-α-responsive PAI-1 promoter activity as well as PAI-1 messenger RNA in human lung epithelial A549 and HeLa cells (FIG. 2c, 2d). Consistent with these results, siCYLD enhanced, whereas overexpressing WT-CYLD, inhibited TGF-β-induced SBE-dependent promoter activity in a dose-dependent manner (FIG. 2e). We next confirmed this finding in human primary bronchial epithelial NHBE cells. As shown in FIG. 2f, siCYLD enhanced, whereas overexpressing WT-CYLD inhibited, TGF-β-induced SBE-Luc activity in NHBE cells. Consistent with the results obtained using siCYLD, CYLD deficiency also enhanced TGF-α-induced SBE-Luc activation in Cyld−/− mouse embryonic fibroblast (MEF) cells as compared with WT MEF (FIG. 2g). Moreover, CYLD deficiency also markedly enhanced induction of TGF-regulated fibrogenic genes in mouse lung tissue, including PAI-1 and CTGF (FIG. 2h). We conclude from these data that CYLD negatively regulates TGF-β-signalling both in vitro and in vivo. We further investigated whether CYLD deficiency leads to lung fibrosis via enhancement of TGF-β-signalling by using SB431542, a specific inhibitor of TGF-β-signalling. Indeed, as shown in FIG. 2i, systemic inoculation of SB431542 inhibited lung fibrosis in *S. pneumoniae*-inoculated Cyld−/− lungs, thereby confirming that CYLD deficiency leads to pulmonary fibrosis in post bacterial infections via enhancing TGF-β-signalling.

Example 9. CYLD Inhibits TGF-β-Signalling Via Decreasing Smad3 Stability

Having identified CYLD as a negative regulator of TGF-β-signalling and lung fibrosis, we next sought to determine how CYLD inhibits TGF-β-signalling. TGF-β-ligands bind to a type II receptor (TβRII), which recruits and phosphorylates a type I receptor (TβRI). The activated TβRI then phosphorylates the Smad subgroup known as receptor-activated Smads (R-Smad), for example, Smad3, which can bind to Co-Smad Smad4. The R-Smad and Co-Smad complex then undergoes nuclear translocation for target gene regulation. To first determine at which level CYLD inhibits TGF-β-signalling, we took advantage of the available lung epithelial cell lines, DR26 and R1B that are derived from the WT Mv1Lu cells and lack functional TβR and TβRI, respectively. As shown in FIG. 3a, siCYLD markedly enhanced constitutively active (C/A)-TβRI-induced SBE-Luc activity in TβRII-deficient DR26 cells, suggesting enhancement of TGF-β-signalling, by CYLD knockdown, occurs at the level or downstream of TβRI independent of TβRII. We next determined whether CYLD exerts its inhibitory effect on TGF-β-signalling at the level or downstream of TβRI by assessing the effects of siCYLD on WT-Smad3-induced SBE-Luc activity in TβRI-deficient R1B cells. CYLD knockdown markedly enhanced WT-Smad3-induced SBE-Luc activation in R1B cells, suggesting CYLD may inhibit TGF-β-signalling at the level or downstream of Smad3 independent of TβRI (FIG. 3b). To further determine whether CYLD inhibits TGF-β-signalling by likely targeting Smad3, we next evaluated the effect of CYLD knockdown in Smad3-deficient MEF cells. As shown in FIG. 3c, siCYLD did not enhance SBE-Luc activity in the absence of Smad3. In contrast, siCYLD markedly enhanced SBE-Luc activity in cells reconstituted with WT-Smad3, suggesting CYLD may inhibit TGF-β-signalling at the level of, or downstream of, Smad3.

To further determine how CYLD inhibits TGF-β-signalling via Smad3, we next evaluated the effect of CYLD on Smad3 activation by using an antibody against phosphorylated Smad3. Interestingly, CYLD knockdown increased, whereas overexpressing WT-CYLD, inhibited not only phosphorylated but also total Smad3 (FIG. 3d). Smad3 expression is also higher in both Cyld−/− MEF and Cyld−/− mouse lung compared with their WT counterparts (FIG. 3e), whereas another R-Smad Smad2 expression was unaffected by CYLD deficiency (FIG. 3f). Consistent with these results, Smad3 expression was also higher in the lung of human patients with pulmonary fibrosis as compared with normal control (FIG. 3g).

Moreover, overexpressing WT-CYLD markedly reduced expression of both endogenous and exogenous Smad3, but not Smad4 proteins (FIG. 3h), but had no effect on the levels of Smad3 mRNA (FIG. 3i). Interestingly, treatment with MG132, a specific proteasome inhibitor, reversed the WT-CYLD-induced decrease in Smad3 protein level (FIG. 3j) and TGF-β-induced PAI-1 expression (FIG. 3k). Collectively, these data suggest that CYLD inhibits TGF-β-signalling by decreasing stability of Smad3 protein in a proteasome-dependent manner.

Example 10. CYLD Decreases Smad3 Stability Via Akt-GSK3β-CHIP Pathway

Because CYLD is a known deubiquitinating enzyme (DUB), we investigated whether CYLD-induced Smad3 degradation depends on its deubiquitinating activity. We first assessed the effect of DUB-deficient CYLD mutants on Smad3 basal level and TGF-β-induced SBE promoter activity. As shown in FIG. 4a, DUB deficient CYLD mutants (H/N-CYLD and C/S-CYLD) failed to induce Smad3 degradation as compared with WT-CYLD. A similar result was also observed in TGF-β-induced SBE promoter activity (FIG. 4b). These data suggest that CYLD decreases Smad3 stability in a DUB activity-dependent manner.

Because E3 ubiquitin ligase has a critical role in mediating Smad3 degradation and CYLD is known as a deubiquitinase, we hypothesized that CYLD may decrease Smad3 stability via regulating an E3 ubiquitin ligase. On the basis that carboxy terminus of CHIP has been shown to mediate Smad3 degradation, we first determined whether CHIP mediates CYLD-induced Smad3 degradation by using siCHIP. The efficiency of siCHIP in reducing CHIP expression was first confirmed in A549 cells. As shown in FIG. 4c, CHIP knockdown using siCHIP reversed the WT-CYLD-induced Smad3 decrease in A549 cells. Similar results were also observed in TGF-β-induced SBE promoter activity and PAI-1 upregulation (FIG. 4d, 4e, respectively). We next examined whether CYLD directly interacts with CHIP by performing co-immunoprecipitation experiments. No direct physical interaction was observed between CYLD and CHIP, thereby suggesting that CYLD may regulate CHIP-dependent Smad3 stability probably by targeting an upstream molecule of CHIP.

In view of the known upstream signalling, molecules involved in mediating Smad3 degradation, GSK3β was shown to have an important role in mediating Smad3 degradation. We thus determined whether GSK3β is involved in mediating CYLD-induced Smad3 degradation. As shown in FIG. 4f, a specific GSK3β inhibitor SB216763 reversed the WT-CYLD-induced Smad3 decrease in A549 cells. Similar results were also observed in TGF-β-induced SBE promoter activity (FIG. 4g), thereby suggesting the involvement of GSK3β in mediating regulation of Smad3 stability by CYLD. We further performed co-immunoprecipitation experiments to determine whether GSK3β directly interacts with CYLD. No direct interaction was found between GSK3β and CYLD, suggesting the involvement of an additional signalling molecule, further upstream of GSK3β. It is interesting to note that GSK3β was found to directly interact with CHIP both in vitro and in vivo (FIG. 4h, 4i). Further experiments demonstrate that GSK3β phosphorylation was induced by S. pneumoniae and enhanced by CYLD deficiency (FIG. 4j, 4k). As phosphorylation of GSK3β is known to result in inactivation of its kinase activity and CYLD deficiency enhances GSK3β phosphorylation, we expected that CYLD may induce GSK3β kinase activity by inhibiting its phosphorylation and thereby promoting GSK3β-CHIP-mediated Smad3 protein degradation. However, it still remains unclear how GSK3β regulates CHIP-mediated Smad3 protein degradation. Previously, it has been reported that Erk5 MAPK regulates E3 ligase activity of CHIP dependently on Erk5 kinase activity. Thus, it is likely that GSK3β may regulate E3 ligase activity of CHIP by binding to CHIP dependently on GSK3β kinase activity. Further investigation is needed for understanding the molecular mechanism underlying GSK3β-mediated regulation of CHIP E3 ligase activity.

We next sought to determine the direct molecular target of CYLD in mediating GSK3β-dependent Smad3 protein degradation. Because Akt is known as the major upstream regulator of GSK3β, we investigated whether Akt mediates CYLD-induced degradation of Smad3. We first determined whether S. pneumoniae induces activation of Akt. As shown in FIG. 4j, S. pneumoniae induced phosphorylation of Akt and GSK3β, but not p70S6K, which represents another downstream target of PI3K pathway, suggesting the specific activation of Akt-GSK3β by S. pneumoniae. Consistent with these results, S. pneumoniae also upregulated Smad3 protein expression in a time-dependent manner (FIG. 4m). This interesting result thus led us to determine whether Akt is critically involved in mediating CYLD-induced degradation of Smad3 by first examining the effect of Akt knockdown on Smad3 protein stability.

Example 11. CYLD Decreases Smad3 Stability by Inhibiting Akt

We found that Akt1 and 2 but not 3 are predominantly expressed in both Cyld+/+ and Cyld−/− cells. Thus, we determined the effect of knockdown of both Akt1 and 2 on Smad3 protein level in these cells. As shown in FIG. 5a, knockdown of Akt1/2 significantly reduced Smad3 protein expression in both WT and Cyld-deficient cells. Consistent with this result, Akt knockdown also inhibited the enhancement of TGF-β-induced SBE promoter activity induced by CYLD knockdown (FIG. 5b). Similarly, enhanced TGF-β-induced SBE promoter activity was also inhibited by Akt-specific inhibitor in Cyld−/− MEFs (FIG. 5c). Moreover, TGF-β-induced PAI-1mRNA expression was also markedly reduced by Akt1-deficiency in Akt1−/− cells, and siCYLD no longer enhanced TGF-β-induced PAI-1 expression in Akt1−/− cells. We further confirmed whether activation of Akt does induce upregulation of fibrotic response gene expression via Smad3. Activation of Akt by expressing a constitutively active C/A-Akt indeed induced expression of PAI-1 and CTGF in Smad3+/+ cells, but not in Smad3−/− cells. Together, these data provide supportive evidence for the critical involvement of Akt in mediating CYLD-dependent Smad3 degradation. PI3 K is known as the one of the major signalling molecules upstream of Akt. We thus determined whether PI3K, like Akt, is also involved in mediating CYLD-dependent Smad3 degradation by evaluating the effect of PI3K and Akt inhibitors on Smad3 protein expression. Akt inhibitor markedly reduced Smad3 protein expression whereas PI3K inhibitor LY294002 did not reduce Smad3 protein expression (FIG. 5d, 5e). These results are rather unexpected as it is well known that PI3K and, in turn, PIP3 is c completely rate-limiting for Akt activation. Because only chemical inhibitors for PI3K were used in our studies, our data do not completely preclude the possible involvement of PI3K in regulating Akt-mediated regulation of Smad3. Further studies are needed to determine whether CYLD-Akt-mediated regulation of Smad3 is indeed independent of PI3K by using more specific approaches. Nonetheless, these data suggest that CYLD decreases Smad3 protein stability via negatively regulating Akt.

To further determine how CYLD negatively regulates Akt, we first examined whether CYLD physically interacts with Akt by performing co-immunoprecipitation experiments. Results in FIG. 5f showed that CYLD and Akt are indeed physically associated with each other in epithelial cells co-transfected with HA-CYLD and Flag-Akt. We next determined whether endogenous CYLD directly interacts with endogenous Akt and if such a direct interaction is further increased on S. pneumoniae treatment by performing Duolink in vivo protein-protein interaction detection assay and co-immunoprecipitation assay. As shown in FIG. 5g, 5h, endogenous CYLD indeed directly interacts with endogenous Akt and S. pneumoniae treatment increased their direct interaction. Together, these data suggest that CYLD decreases Smad3 stability and TGF-β-signalling by inhibiting Akt.

Example 12. CYLD Deubiquitinates K63-Ubiquitinated Akt to Inhibit Smad3

We next investigated whether CYLD deubiquitinates Akt. As shown in FIG. 6a, co-expressing WT-CYLD, but not DUB mutant (H/N-CYLD), decreased Akt polyubiquitination. In addition, siCYLD also markedly enhanced S. pneumoniae-induced Akt ubiquitination in epithelial cells (FIG. 6b). We then determined whether S. pneumoniae induces endogenous Akt ubiquitination in the absence and presence of CYLD. As shown in FIG. 6c, 6d, endogenous Akt ubiquitination was detected in the absence of S. pneumoniae, and S. pneumoniae markedly enhanced endogenous Akt ubiquitination. Interestingly, expression of WT-CYLD greatly decreased S. pneumoniae-induced endogenous Akt ubiquitination, whereas CYLD knockdown, or CYLD deficiency, enhanced it. Because Akt has been shown to undergo K63 polyubiquitination, we next determined whether CYLD specifically deubiquitinates K63-polyubiquitinated Akt. As shown in FIG. 6e, co-expressing WT-CYLD markedly decreased K63- but not K48-polyubiquitinated Akt. Consistently, results in FIG. 6f indicate that recombinant CYLD protein (GST-rCYLD) directly deubiquitinates K63-linked polyubiquitination of Akt (HisrAkt) in vitro in a cell-free system in a dose-dependent manner. Moreover, deficiency of CYLD also enhanced S. pneumoniae-induced K63-polyubiquitination of Akt (FIG. 6g). Taken together, these data provide strong evidence that CYLD negatively regulates Akt by directly interacting with and deubiquitinating K63-polyubiquitinated Akt, both in vitro in a cell-free system and in vivo under endogenous conditions.

Because K14 lysine in the pleckstrin homology domain of Akt is critical for mediating its function, we next determined whether mutation of K14 lysine to arginine (R) reduces polyubiquitination of Akt. Indeed, K14R, but not K8R, K20R and K30R, markedly reduced K63-linked polyubiquitination of Akt compared with WT-Akt (FIG. 6h). We further determined whether K14 residue in Akt is indeed functionally critical for mediating CYLD-induced inhibition of TGF-β-signalling. As shown in FIG. 6i, expressing WT-CYLD significantly inhibited TGF-β-induced SBE promoter activity in epithelial cells co-transfected with WT-Akt or K20R, but not with K14R, thereby demonstrating the critical role for K14 in the PH domain of Akt in mediating inhibition of TGF-β-signalling by CYLD. TNF receptor-associated factor 6 (TRAF6) was previously shown to function as an E3 ligase for Akt-K63 polyubiquitination and CYLD deubiquitinates TRAF6. Thus, we next explored the possibility that CYLD may inhibit Akt-mediated fibrotic responses via deubiquitinating TRAF6. CYLD knockdown, using siCYLD, still enhanced TGF-β-induced fibrotic response in TRAF6-depleted cells, thereby suggesting that CYLD inhibits Akt-mediated fibrotic responses at least in part by directly interacting with and deubiquitinating Akt.

Comments:

In the present study, we provide evidence to identify CYLD deubiquitinase as a critical negative regulator for preventing development of lung fibrosis after infection with S. pneumoniae. CYLD inhibits TGF-β-signalling and thereby prevents fibrosis via decreasing stability of Smad3 protein in a GSK3β-CHIP-dependent manner. Moreover, CYLD decreases Smad3 protein stability by directly deubiquitinating K63-polyubiquitinated Akt, which, in turn, leads to activation of GSK3β (FIG. 7a). CYLD deficiency results in enhanced fibrotic response via enhanced Smad3-protein stability following lung injury (FIG. 7b). CYLD promotes bacteria-induced lung injury and reduces host survival by inhibiting S. pneumoniae-induced PAI-1 expression via specific inhibition of p38 signalling during early lung-injury stage of infection; and as shown in our current study, CYLD prevents the development of lung fibrosis by inhibiting TGF-β-Smad signalling via reducing Smad3 stability during late tissue remodelling stage of infection. Thus, CYLD acts a key regulator during the entire wound-healing process in lung injury.

Previously, was suggested that TNF receptor-associated factor 6 (TRAF6) acts as an E3 ligase for Akt-K63 polyubiquitination, and CYLD deubiquitinates TRAF6. In this study we provided experimental evidence for a direct interaction between Akt and CYLD, and also showed that CYLD does directly deubiquitinate Akt under both endogenous and exogenous conditions. It is possible that CYLD may inhibit Akt-mediated fibrotic response by actually deubiquitinating TRAF6. Thus, we evaluated the effect of siCYLD on TGF-β-induced fibrotic response in TRAF6-depleted cells using siTRAF6. Interestingly, CYLD knockdown still led to the enhancement of TGF-β-induced fibrotic response in TRAF6-depleted cells. Nonetheless, these data demonstrate that CYLD indeed inhibits Akt-mediated fibrotic response by at least in part directly interacting with and deubiquitinating Akt. Here we have provided strong evidence that CYLD inhibits *S. pneumoniae*-induced Smad3-dependent fibrosis via inhibiting Akt, thereby linking CYLD to Smad3 via Akt. It is still unclear whether or not direct activation of Akt induces a fibrotic response via Smad3. Indeed, direct activation of Akt by expressing a constitutively active form of C/A-Akt induces expression of the fibrotic response gene PAI-1 and CTGF in Smad3+/+ cells, but not in Smad3−/− cells. Collectively, it is evident that the fibrotic effects of CYLD-dependent Akt deubiquitination are indeed specifically mediated via the TGF-β-Smad3 pathway.

On the basis of the experimental data we presented, it is clear that CYLD regulates lung fibrosis by inhibiting TGF-β-signalling in wound-healing response in lung injury caused by infectious agents. Because TGF-β-signalling has an essential role in regulating the tissue fibrotic response, we believe that CYLD will also be crucial for negatively regulating fibrotic responses induced by other injurious stimuli such as caustic chemicals. Thus, we sought to determine whether CYLD also acts as a key negative regulator for chemical-induced lung fibrosis in a widely used lung fibrosis model induced by bleomycin. Interestingly, CYLD deficiency markedly enhanced bleomycin-induced lung fibrosis in Cyld-deficient mice. These data thus suggest that the inhibitory effect of CYLD in fibrotic responses may be generalizable for tissue fibrosis induced not only by infectious agents but also by other injurious stimuli such as caustic chemicals, as long as the fibrotic response is mainly mediated via TGF-β-Smad signaling.

Methods.

The methods described below were useful in carrying out the studies described above, and one of ordinary skill in the art will recognize that some or all of these methods (e.g., the production of nucleic acid constructs and nucleic acids that mediate RNAi) are useful in practicing the invention as set out herein.

Cell Culture and Reagents.

A549, HeLa and HEK293 cells were maintained in the F12-K, minimal essential medium Eagle's with Earle's balanced salt solution (EMEM), and DMEM scintillant. WT mink MvlLu cells and two mutant cell lines DR26 and R1B cells were maintained with EMEM supplemented with non-essential amino acids. MEFs from Smad3−/−, Cyld+/+ and Cyld−/− mice were maintained in DMEM. Human primary bronchial epithelial NHBE (Cambrex) cells were maintained in bronchial epithelial growth media supplemented with bronchial epithelial growth media single Quot. Recombinant TGF-β1 (indicated as TGF-β above) and TNF-α were purchased from R & D system; Akt inhibitor (1L6-Hydroxymethyl-chiro-inositol-2(R)-2-O-methyl-3-O-octadecyl-sn-glycerocarbonate) and SB203580 were from Calbiochem; SB431542 and bleomycin were from Sigma; MG132 was from American Peptide. In vitro ubiquitination and deubiquitination assay kit was purchased from Boston Biochem. Duolink in vivo protein-protein interaction detection assay kit was from Olink Bioscience. Recombinant His-Akt and His-GSK3β were from Calbiochem. ELISA assay kits for TGF-β and total and phospho-p38 MAPK were purchased from R&D system and Invitrogen, respectively.

Real-Time Quantitative RT-PCR Analysis.

Total RNA was isolated using TRIzol reagent following the manufacturer's instructions. Synthesis of complementary DNA from total RNA was performed with MultiScribe reverse transcriptase. Real-time quantitative PCR was performed using an ABI 7500 Sequence Detection System (Applied Biosystems). Relative quantities of mRNAs were calculated using the comparative threshold cycle method and normalized using human and mouse glyceraldehyde-3-phosphate dehydrogenase as an endogenous control. The primer sequences for mouse COL1A2, COL3A1, CTGF and PAI-1, and human PAI-1, CHIP, and Smad3 are as follows. Mouse CTGF: 5'-GTAACCGGGGA GGGAAATTA-3' (SEQ ID NO:1) and 5'-ACAGCTGGACTCAGCCTCAT-3' (SEQ ID NO:2); mouse COL1A2: 5'-GACAAAT-GAATGGGGCAAG-3' (SEQ ID NO:3) and 5'-CAATGTC-CAGAGGTGCAATG-3' (SEQ ID NO:4); mouse COL3A1: 5'-CGAAGATGGCAAAGATGGAT-3' (SEQ ID NO:5) and 5'-GCCACTAGGACCCCTTTCTC-3' (SEQ ID NO:6); mouse PAI-1: 5'-GTAGCACAGGCACTGCAAAA-3' (SEQ ID NO:7) and 5'-TGAGATGACAAAGGCTGTGG-3' (SEQ ID NO:8); human PAI-1: 5'-CCCTTTGCAG GATG-GAACTA-3' (SEQ ID NO:9) and 5'-ATGGCAATGT-GACTGGAACA-3' (SEQ ID NO:10); human CHIP: 5'-CCCGGCCCCTATACATAGTT-3' (SEQ ID NO:11) and 5'-CAGTCCAGAGTCCAACAGCA-3' (SEQ ID NO:12).

Plasmids, Transfections, and Luciferase Assays.

The expression plasmids Flag-WT-CYLD, HA-WT-CYLD, Flag-H/N-CYLD, HA-C/S-CYLD, Flag-WT-Smad3, C/A-TβRI, and the reporter plasmids SBE-Luc, PAI-1-Luc, and NF-κB-Luc were previously described. Flag-WT-Akt1, pRK5-HA-Ub WT, pRK5-HA-Ub K63, and pRK5-HA-Ub K48 were from Addgene, and K to R mutants of Akt were generated with WT-Akt1 using QuickChange XL Site-Directed Mutagenesis kit (Stratagene). All transient transfections were carried out using TransIT-LT1 reagent (Minis) or Lipofectamine (Invitrogen) according to manufacturers' instructions.

RNA-Mediated Interference.

RNA-mediated interference for downregulating CYLD expression was carried out using pSuper-CYLD and the sequence for the siCYLD is 5'-GATCCCCGAGCTACT-GAGGACAGAAATTCAAGAGATTTCTGTCCTCAG-TAG CTCTTTTTGGAAA-3' (SEQ ID NO:13). Human and mouse siRNAs for Akt and CHIP were from Dharmacon, and knockdown of Akts and CHIP, using siAkt and siCHIP, was performed with Lipofectamine 2000 (Invitrogen). ON-TARGETplus SMARTpool of siRNAs targeting human Akt1, human CHIP, mouse Akt1, and mouse Akt2 consists of four siRNAs and sequences for the siRNAs are as follows: Human siAkt1 (5'-CAUCACACCACCUGAC-CAA-3' (SEQ ID NO:14), 5'-ACAAGGACGGGCA-CAUUAA-3' (SEQ ID NO:15), 5'CAAGGGCACUUUCG-GCAAG-3' (SEQ ID NO:16), 5'-UCACAGCCCUGAAGUACUC-3' (SEQ ID NO:17)); human CHIP (5'-CGCUGGUGGCCGUGUAUUA-3' (SEQ ID NO:18), 5'-GUGGAGGACUACUGAGGUU-3' (SEQ ID NO:19), 5'-GAAGGAGGUUAUUGACGCA-3' (SEQ ID NO:20), 5'-UGGAAGAGUGCCAGCGAAA-3' (SEQ ID NO:21)); mouse Akt1 (5'-CUGCAGAACUCUAG-GCAUC-3' (SEQ ID NO:22), 5'-GAUCAAGGAUGGUGC-CACU-3' (SEQ ID NO:23), 5'-GAGGUUGCCCACACGC-UUA-3' (SEQ ID NO:24), 5'-CGACGUAGCCAUUGUGAAG-3' (SEQ ID NO:25)); mouse Akt2 (5'-CCAUGAAUGACUUCGAUUA-3' (SEQ ID NO:26), 5'-GUACUUUGAUGACGAGUUC-3' (SEQ ID NO:27), 5'-CCUGAACAAUUUCUCUGUA-3' (SEQ ID NO:28), 5'-GAUGCGGGCUAUCCAGAUG-3' (SEQ ID NO:29)).

Western Blot, Immunoprecipitation, and Ubiquitination Experiments.

Western blot, immunoprecipitation and ubiquitination experiments were performed as follows. Western blots were performed using whole-cell extracts, separated on 8 or 10% SDS-PAGE gels, and transferred to polyvinylidine di&uoride membranes. The membrane was blocked with a solution of PBS containing 0.1% Tween 20 (PBS-T) and 5% BSA. The membrane was then incubated in a 1:2,000 dilution of a primary antibody in 5% BSA-PBS-T. After three washes in PBS-T, the membrane was incubated with 1:5,000 dilution of the corresponding secondary antibody in 3% non-fact skim milk-PBS-T. Respective proteins were visualized by using enhanced chemiluminescence detection reagents, according to the manufacturer's instructions. To conduct immunoprecipitation analysis, cell lysates were incubated with 1 µg of primary antibodies overnight, at 4° C., followed by 2-h incubation with protein A/G-agarose beads (Invitrogen). Immunoprecipitates were then suspended in a sample buffer, separated on 8% SDS-PAGE, transferred to polyvinylidine difluoride membrane, and detected by immunoblot analysis, as described above. The antibodies against total-Akt, phospho-Akt at T308 & S473, total Smad3, phospho-Smad3, total p70S6K, phospho-p70S6K at T389, total GSK3β, phospho-GSK3β at S9, mouse HA-Tag, His-Tag, and mouse and rabbit anti-Ubiquitin were purchased from Cell Signaling; antibodies against CYLD, total-Akt1/2/3, goat total-Akt1, Smad4, rabbit HA-Tag, mouse Ubiquitin, and actin were from Santa Cruz; FLAG and β-actin were from Sigma.

In Vivo Protein-Protein Interaction Detection Assay.

A549 cells were cultured on tissue culture slides and incubated with *S. pneumoniae* or control for the time indicated in the figures/drawings. Cells were stained with 2 µg ml-1 of primary mouse anti-Akt antibody and rabbit anti-CYLD antibody, and protein-protein interaction between Akt and CYLD was detected with secondary proximity probes, anti-Rabbit MINUS and anti-mouse PLUS, using Duolink in vivo protein-protein interaction detection assay kit, according to the manufacturer's instructions (Duolink proximity ligation assay, Olink Bioscience).

Mice and Animal Experiments.

Cyld−/− mice were generated by homologous recombination as follows. The targeting construct was designed to disrupt the exons 2 and 3 with an IRES-LacZ/MC1-Neo cassette. The targeting plasmid was linearized and transfected into embryonic stem cells of a 129/S. Homologously recombined embryonic stem cells were injected into blastocysts that were subsequently transferred to foster mothers, to generate chimeric progeny. Generated chimeric progeny were backcrossed to C57BL/6J, and germline transmission was confirmed by PCR with tail DNA. Homozygous knockout of Cyld gene was confirmed by mRNA detection by RT-PCR and CYLD protein detection by western blot analysis in MEF cells and lung tissues. For *S. pneumoniae*-induced severe infections in WT and Cyld−/− mice, anaesthetized mice were intratracheally (i.t.) inoculated with live *S. pneumoniae* ($5 \times 10^7$ CFU per mouse). Surviving mice from severe pneumonia were then sacrificed 2 weeks post *S. pneumoniae* infection for histopathological analysis. For TGF-β inoculation, anesthetized WT and Cyld−/− mice were i.t. inoculated with TGF-β (25-100 ng per mouse) for 6 hours, and lung tissues were then subjected to total mRNA and protein extraction. In experiments using chemical inhibitor, SB431542 (10 mg kg-1) or SB203580 (20 mg $kg^{-1}$) or an equal volume of vehicle control was administered via an intraperitoneal route 1-2 hours before the i.t. inoculation of *S. pneumoniae*. For the bleomycin-induced fibrosis model, animals were i.t. inoculated with bleomycin (3 units per kg body weight) for 2 weeks. Lung tissues were then subjected to histological analysis and total mRNA and protein extraction. All animal experiments were approved by the Institutional Animal Care and Use Committee (IACUC) at University of Rochester and Georgia State University.

Cyld−/− mice and normal control and pulmonary fibrosis patients were stained with haematoxylin and eosin (H & E), to visualize lung inflammation, and Masson's trichrome staining (Trichrome staining) was performed to highlight organizing fibrosis. Immunohistochemical staining against CYLD and Smad3 was performed using ABC staining System (Santa Cruz). Briefly, tissue sections were incubated with 1 µg of primary antibody or control IgG followed by 3 washes with PBS. Tissues were then incubated with 1 µg of biotinylated secondary antibodies followed by the incubation with AB enzyme reagent. After three washes, colour reaction was developed with peroxidase substrate. Control and fibrotic lung tissues from patients were obtained from Chonnam National Hospital with approval from the Institutional Review Board (IRB) at Chonnam National University, Korea.

Example 13. PDE4B Mediates *S. pneumoniae*-Induced Mucin MUC5AC Expression by Inhibiting Expression of MKP-1, which in Turn Leads to the Enhanced Activation of MAPK ERK Having demonstrated a critical role for PDE4 in regulating MUC5AC induction (data not shown), we next sought to determine which PDE4 subfamily member is specifically involved. PDE4 consists of 4 subfamily genes, PDE4A to D, encoding rolipram-sensitive PDEs. We first determined if PDE4 is up-regulated by *S. pneumoniae*. PDE4B, but not A, is markedly up-regulated by *S. pneumoniae* as assessed using Q-PCR in human middle ear HMEEC cells. A similar result was also observed in the middle ear mucosa of mouse as well as in human primary NHBE cells and airway epithelial cell line A549. In addition, up-regulation of PDE4B by *S. pneumoniae* at the protein level was observed in HMEEC cells as assessed by performing Western Blot analysis. Consistent with these results, PDE4 enzymatic activity was also up-regulated by *S. pneumoniae*. Together, these data suggest that PDE4B may play an important role in regulating *S. pneumoniae*-induced mucin MUC5AC up-regulation. To further explore if PDE4B is required, we next performed siRNA knockdown of PDE4B. Small interfering RNA (siRNA) for PDE4B was purchased from Dharmacon (Lafayette, Colo.). The siRNA was transfected into epithelial cells using Lipofectamine 2000 (Invitrogen, Grand Island, N.Y.) following the manufacturer's instructions and as described previously (Ha et al., *J. Immunol.* 178:1736-1747, 2007; Ishinaga et al., *Biochem. J.* 417:583-591, 2009; Lim et al., *Cell Microbiol.* 10:2247-2256, 2008; Lim et al., *PLoS One* 2, e1032, 2007). We first determined the efficiency of PDE4B-siRNA in reducing PDE4B expression. PDE4B expression was markedly reduced by PDE4B-siRNA. Next, we determined the effect of PDE4B-siRNA. PDE4B-siRNA markedly inhibited *S. pneumoniae*-induced up-regulation of MUC5AC at the mRNA level in human middle ear epithelial HMEEC cells. Furthermore, knockdown of PDE4B using PDE4B-siRNA significantly enhanced *S. pneumoniae*-induced MKP-1 mRNA expression. Taken together, these data provide direct evidence that PDE4B plays an important role in regulating *S. pneumoniae*-induced up-regulation of mucin MUC5AC via inhibiting MKP-1.

What is claimed is:

1. A method of treating a patient who is suffering from inflammation within, or mucus overproduction within, either ear or both ears, the method comprising administering to the patient a therapeutically effective amount of a pharmaceutical composition comprising a single active agent that upregulates the activity of the deubiquitinase encoded by the gene cylindromatosis (CYLD).

2. The method of claim 1, wherein the patient is suffering from otitis media or an infectious disease that causes inflammation within either ear or both ears.

3. The method of claim 1, wherein the patient is an infant or child.

4. The method of claim 1, wherein the agent is rolipram, roflumilast, cilomilast, a compound consisting of a substituted benzene ring, or a compound comprising a substituted six-membered heteroaryl ring comprising one or two ring nitrogens, the substitution on the substituted benzene ring or the substituted six-membered heteroaryl ring is an ether, thioether, or amine group, wherein the ether, thioether, or amine includes a haloalkyl group.

5. The method of claim 1, wherein the agent selectively inhibits a PDE4B isoform of PDE4.

6. The method of claim 1, wherein the pharmaceutical composition is formulated for ototopic administration.

7. The method of claim 1, wherein the patient is a human.

8. The method of claim 1, wherein the patient is a domesticated pet.

9. The method of claim 1, wherein the agent is rolipram.

10. The method of claim 1, wherein the agent is roflumilast.

11. The method of claim 1, wherein the agent is cilomilast.

* * * * *